United States Patent
Gross et al.

(10) Patent No.: US 12,208,267 B1
(45) Date of Patent: Jan. 28, 2025

(54) BLOOD FLOW ENHANCEMENT THERAPY SYSTEM

(71) Applicants: Yossi Gross, Moshav Mazor (IL); Ofri Vaisman, Sunnyvale, CA (US)

(72) Inventors: Yossi Gross, Moshav Mazor (IL); Ofri Vaisman, Sunnyvale, CA (US)

( * ) Notice: Subject to any disclaimer, the term of this patent is extended or adjusted under 35 U.S.C. 154(b) by 0 days.

(21) Appl. No.: 18/640,726

(22) Filed: Apr. 19, 2024

(51) Int. Cl.
*A61N 1/36* (2006.01)
*A61N 1/04* (2006.01)
*A61N 1/05* (2006.01)
*A61N 1/39* (2006.01)

(52) U.S. Cl.
CPC ........ *A61N 1/36114* (2013.01); *A61N 1/0456* (2013.01); *A61N 1/0546* (2013.01); *A61N 1/0548* (2013.01); *A61N 1/0558* (2013.01); *A61N 1/3603* (2017.08); *A61N 1/3987* (2013.01)

(58) Field of Classification Search
CPC . A61N 1/36114; A61N 1/3603; A61N 1/0456
USPC .......................................................... 607/7
See application file for complete search history.

(56) References Cited

U.S. PATENT DOCUMENTS

| | | | |
|---|---|---|---|
| 4,044,774 A | 8/1977 | Corbin et al. | |
| 4,503,863 A | 3/1985 | Katims | |
| 5,088,977 A | 2/1992 | Sibalis | |
| 5,121,754 A | 6/1992 | Mullett | |
| 5,433,739 A | 7/1995 | Sluijter et al. | |
| 5,529,574 A | 6/1996 | Frackelton | |
| 5,792,100 A | 8/1998 | Shantha | |
| 5,911,223 A | 6/1999 | Weaver et al. | |
| 5,938,690 A | 8/1999 | Law et al. | |
| 6,041,252 A | 3/2000 | Walker et al. | |
| 6,146,380 A | 11/2000 | Racz et al. | |
| 6,161,047 A | 12/2000 | King et al. | |
| 6,360,750 B1 | 3/2002 | Gerber et al. | |
| 6,526,318 B1 | 2/2003 | Ansarinia | |

(Continued)

FOREIGN PATENT DOCUMENTS

| | | |
|---|---|---|
| JP | 2004-321242 | 11/2004 |
| JP | 2007-501067 | 1/2007 |

(Continued)

OTHER PUBLICATIONS

United States Office Action issued Dec. 13, 2023 in U.S. Appl. No. 18/229,379.

(Continued)

*Primary Examiner* — Nadia A Mahmood
(74) *Attorney, Agent, or Firm* — Sughrue Mion, PLLC

(57) ABSTRACT

A sphenopalatine ganglion (SPG) stimulating device for stimulating an SPG of a patient is provided. The SPG stimulating device includes a sheath having a proximal end portion and a distal end portion, the distal end portion shaped to define at least one electrode opening. A nasal stabilizer is disposed around the sheath and configured to stabilize the sheath with respect to a nostril of a nose of the patient when the sheath is disposed within the nose. An electrode mount is slidably disposed within the sheath, and at least one electrode is coupled to the electrode mount and deployable out of the sheath through the at least one electrode opening to position the at least one electrode to stimulate the SPG. Other applications are also described.

45 Claims, 19 Drawing Sheets

(56) References Cited

U.S. PATENT DOCUMENTS

| | | |
|---|---|---|
| 6,567,702 B1 | 5/2003 | Nekhendzy et al. |
| 6,591,138 B1 | 7/2003 | Fischell et al. |
| 6,602,248 B1 | 8/2003 | Sharps et al. |
| 6,620,155 B2 | 9/2003 | Underwood et al. |
| 6,941,172 B2 | 9/2005 | Nachum |
| 6,997,941 B2 | 2/2006 | Sharkey et al. |
| 7,013,177 B1 | 3/2006 | Whitehurst et al. |
| 7,117,033 B2 | 10/2006 | Shalev et al. |
| 7,120,489 B2 | 10/2006 | Shalev et al. |
| 7,146,209 B2 | 12/2006 | Gross et al. |
| 7,217,351 B2 | 5/2007 | Krumme |
| 7,223,227 B2 | 5/2007 | Pflueger |
| 7,270,659 B2 | 9/2007 | Ricart et al. |
| 7,317,947 B2 | 1/2008 | Wahlstrand et al. |
| 7,398,121 B2 | 7/2008 | Matsumura et al. |
| 7,509,171 B2 | 3/2009 | DiMauro |
| 7,561,919 B2 | 7/2009 | Shalev et al. |
| 7,636,597 B2 | 12/2009 | Gross et al. |
| 7,640,062 B2 | 12/2009 | Shalev |
| 7,684,859 B2 | 3/2010 | Shalev et al. |
| 7,818,063 B2 | 10/2010 | Wallace et al. |
| 7,831,306 B2 | 11/2010 | Finch et al. |
| 7,860,569 B2 | 12/2010 | Solberg et al. |
| 8,055,347 B2 | 11/2011 | Lamensdorf et al. |
| 8,060,207 B2 | 11/2011 | Wallace et al. |
| 8,103,350 B2 | 1/2012 | Wallace et al. |
| 8,190,248 B2 | 5/2012 | Besio et al. |
| 8,287,902 B2 | 10/2012 | Gross |
| 8,353,853 B1 | 1/2013 | Kyle et al. |
| 8,457,761 B2 | 6/2013 | Wariar |
| 8,494,641 B2 | 7/2013 | Boling et al. |
| 8,577,469 B2 | 11/2013 | Gross |
| 8,676,348 B2 | 3/2014 | Gross |
| 8,731,674 B2 | 5/2014 | Wallace et al. |
| 8,954,149 B2 | 2/2015 | Shalev |
| 9,233,245 B2 | 1/2016 | Lamensdorf et al. |
| 9,433,774 B2 | 9/2016 | Dar et al. |
| 9,616,221 B2 | 4/2017 | Gross |
| 9,675,796 B2 | 6/2017 | Dayan et al. |
| 9,724,513 B2 | 8/2017 | Lane et al. |
| 9,724,515 B2 | 8/2017 | Fostick et al. |
| 9,731,122 B2 | 8/2017 | Gross |
| 9,775,996 B2 | 10/2017 | Gross |
| 10,271,907 B2 | 4/2019 | Dayan et al. |
| 10,279,192 B2 | 5/2019 | Malchano et al. |
| 10,293,177 B2 | 5/2019 | Malchano et al. |
| 10,307,611 B2 | 6/2019 | Malchano et al. |
| 10,398,884 B2 | 9/2019 | Lad et al. |
| 10,532,204 B2 | 1/2020 | Gross |
| 10,569,086 B2 | 2/2020 | Fostick et al. |
| 10,695,557 B1 | 6/2020 | Townley et al. |
| 10,758,722 B2 | 9/2020 | Gross et al. |
| 10,881,858 B1 | 1/2021 | Gross et al. |
| 10,898,716 B2 | 1/2021 | Fostick et al. |
| 10,994,132 B1 | 5/2021 | Heldman et al. |
| 11,027,117 B2 | 6/2021 | Dar et al. |
| 11,154,710 B2 | 10/2021 | Belson et al. |
| 11,202,905 B2 | 12/2021 | Tendler et al. |
| 11,376,422 B2 | 7/2022 | Gross |
| 11,413,455 B1 | 8/2022 | Gross |
| 2002/0151948 A1 | 10/2002 | King et al. |
| 2002/0183683 A1 | 12/2002 | Lerner |
| 2003/0130707 A1 | 7/2003 | Gan et al. |
| 2003/0158589 A1 | 8/2003 | Katsnelson |
| 2003/0216792 A1 | 11/2003 | Levin et al. |
| 2003/0225331 A1 | 12/2003 | Diederich et al. |
| 2004/0002746 A1 | 1/2004 | Ryan et al. |
| 2004/0015068 A1 | 1/2004 | Shalev et al. |
| 2004/0019381 A1 | 1/2004 | Pflueger |
| 2004/0049134 A1 | 3/2004 | Tosaya et al. |
| 2004/0049180 A1 | 3/2004 | Sharps et al. |
| 2004/0116977 A1 | 6/2004 | Finch et al. |
| 2004/0210209 A1 | 10/2004 | Yeung et al. |
| 2004/0253304 A1 | 12/2004 | Gross et al. |
| 2005/0010205 A1 | 1/2005 | Hovda et al. |
| 2005/0021104 A1 | 1/2005 | DiLorenzo |
| 2005/0119650 A1 | 6/2005 | Sanders et al. |
| 2005/0137646 A1 | 6/2005 | Wallace et al. |
| 2005/0137647 A1 | 6/2005 | Wallace et al. |
| 2005/0159790 A1* | 7/2005 | Shalev ............... A61M 5/1723 607/45 |
| 2005/0187589 A1 | 8/2005 | Wallace et al. |
| 2005/0203599 A1 | 9/2005 | Garabedian et al. |
| 2005/0203600 A1 | 9/2005 | Wallace et al. |
| 2005/0203602 A1 | 9/2005 | Wallace et al. |
| 2005/0222647 A1 | 10/2005 | Wahlstrand et al. |
| 2005/0266099 A1 | 12/2005 | Shalev |
| 2005/0277996 A1 | 12/2005 | Podhajsky et al. |
| 2006/0030895 A1 | 2/2006 | Simon et al. |
| 2006/0095066 A1* | 5/2006 | Chang ............. A61B 17/12136 606/199 |
| 2006/0106430 A1 | 5/2006 | Fowler et al. |
| 2006/0224223 A1 | 10/2006 | Podhajsky et al. |
| 2006/0293723 A1 | 12/2006 | Whitehurst et al. |
| 2007/0000784 A1 | 1/2007 | Paul et al. |
| 2007/0073402 A1 | 3/2007 | Vresilovic et al. |
| 2007/0162086 A1 | 7/2007 | Dilorenzo |
| 2007/0213700 A1 | 9/2007 | Davison et al. |
| 2007/0233202 A1 | 10/2007 | Wallace et al. |
| 2007/0255338 A1 | 11/2007 | Wahlstrand |
| 2008/0009927 A1 | 1/2008 | Vilims |
| 2008/0033503 A1 | 2/2008 | Fowler et al. |
| 2008/0119907 A1 | 5/2008 | Stahmann |
| 2008/0260542 A1 | 10/2008 | Nishikawa et al. |
| 2008/0275430 A1 | 11/2008 | Belsky et al. |
| 2009/0112278 A1 | 4/2009 | Wingeier et al. |
| 2009/0125080 A1 | 5/2009 | Montgomery |
| 2009/0126813 A1 | 5/2009 | Yanagisawa et al. |
| 2009/0131850 A1 | 5/2009 | Geiger |
| 2009/0210026 A1 | 8/2009 | Solberg et al. |
| 2009/0299418 A1 | 12/2009 | Shalev et al. |
| 2009/0312816 A1 | 12/2009 | Gross |
| 2010/0114184 A1 | 5/2010 | Degtyar et al. |
| 2010/0185258 A1 | 7/2010 | Papay |
| 2010/0217369 A1 | 8/2010 | Gross |
| 2010/0324441 A1 | 12/2010 | Hargrove et al. |
| 2011/0046540 A1 | 2/2011 | Alterman et al. |
| 2011/0054518 A1 | 3/2011 | Carbunaru et al. |
| 2011/0160638 A1 | 6/2011 | Mauge et al. |
| 2011/0160797 A1 | 6/2011 | Makous et al. |
| 2012/0053659 A1 | 3/2012 | Molnar et al. |
| 2012/0071811 A1 | 3/2012 | Ansarinia |
| 2012/0203307 A1 | 8/2012 | Schroeppel et al. |
| 2012/0323214 A1 | 12/2012 | Shantha |
| 2013/0066392 A1 | 3/2013 | Simon et al. |
| 2013/0102952 A1 | 4/2013 | Gross |
| 2013/0150653 A1 | 6/2013 | Borsody |
| 2013/0166006 A1 | 6/2013 | Williams |
| 2013/0184803 A1 | 7/2013 | Altman |
| 2013/0289385 A1 | 10/2013 | Lozano et al. |
| 2014/0058189 A1 | 2/2014 | Stubbeman |
| 2014/0088672 A1 | 3/2014 | Bedenbaugh |
| 2014/0207224 A1 | 7/2014 | Simon |
| 2014/0257168 A1 | 9/2014 | Gill |
| 2014/0324128 A1 | 10/2014 | Gross |
| 2015/0011927 A1 | 1/2015 | Hua |
| 2015/0038948 A1 | 2/2015 | Ludvig et al. |
| 2015/0119898 A1 | 4/2015 | Desalles et al. |
| 2015/0174406 A1 | 6/2015 | Lamensdorf et al. |
| 2016/0331970 A1 | 11/2016 | Lozano |
| 2017/0007823 A1 | 1/2017 | Gross |
| 2017/0056642 A1 | 3/2017 | Moffitt et al. |
| 2017/0120053 A1 | 5/2017 | Fostick et al. |
| 2017/0182317 A1 | 6/2017 | Gross et al. |
| 2017/0296121 A1 | 10/2017 | Dar et al. |
| 2017/0296821 A1 | 10/2017 | Fostick et al. |
| 2018/0071523 A1 | 3/2018 | Gross et al. |
| 2018/0132947 A1 | 5/2018 | Dayan et al. |
| 2018/0193633 A1 | 7/2018 | Gross |
| 2018/0193646 A1 | 7/2018 | Fostick et al. |
| 2018/0318575 A1 | 11/2018 | Gross et al. |
| 2019/0009076 A1 | 1/2019 | Dayan et al. |
| 2019/0076653 A1 | 3/2019 | Fostick et al. |
| 2019/0282807 A1 | 9/2019 | Tendler et al. |

(56) References Cited

U.S. PATENT DOCUMENTS

| | | |
|---|---|---|
| 2019/0290908 A1 | 9/2019 | Hsu et al. |
| 2020/0100838 A1 | 4/2020 | Townley et al. |
| 2020/0171283 A1 | 6/2020 | Tal et al. |
| 2020/0222729 A1 | 7/2020 | Gertner et al. |
| 2020/0297238 A1 | 9/2020 | Tsui |
| 2022/0008746 A1 | 1/2022 | Malchano et al. |
| 2022/0288383 A1 | 9/2022 | Dar et al. |
| 2022/0331594 A1 | 10/2022 | Gross et al. |
| 2023/0022546 A1 | 1/2023 | Malchano et al. |
| 2023/0104621 A1 | 4/2023 | Malchano et al. |
| 2023/0111776 A1 | 4/2023 | Malchano et al. |
| 2023/0166072 A1 | 6/2023 | Malchano et al. |
| 2023/0233858 A1 | 7/2023 | Minar et al. |
| 2023/0381508 A1 | 11/2023 | Ludwig et al. |

FOREIGN PATENT DOCUMENTS

| | | |
|---|---|---|
| WO | 94/05369 | 3/1994 |
| WO | 01/52931 | 7/2001 |
| WO | 01/85027 | 11/2001 |
| WO | 2001/085094 | 11/2001 |
| WO | 2004/044947 A2 | 5/2004 |
| WO | 2004/045242 | 5/2004 |
| WO | 2005/011805 | 2/2005 |
| WO | 2005/030025 A2 | 4/2005 |
| WO | 2005/030118 A2 | 4/2005 |
| WO | 2006/090397 | 8/2006 |
| WO | 2008/007369 | 1/2008 |
| WO | 2009/137683 A2 | 11/2009 |
| WO | 2017/006327 | 1/2017 |
| WO | 2017/072769 | 5/2017 |
| WO | 2017/115351 | 7/2017 |
| WO | 2018/051338 | 3/2018 |
| WO | 2019/175879 A1 | 9/2019 |
| WO | 2022/056310 A1 | 3/2022 |
| WO | 2023/225265 A1 | 11/2023 |

OTHER PUBLICATIONS

United States Office Action issued Feb. 15, 2024 in U.S. Appl. No. 18/229,379.
Karran September E et201 al., 1 "The Amyloid cascade hypothesis for AD," Nature Reviews Drug Discovery, vol. 10; 698-712.
De La Torre JC, "Vascular Basis of Alzheimer's Pathogensis," Ann NY Acad Sci. 977:196-215 (Nov. 2002).
Weller RO et al, "Perivascular Drainage of Amyloid-b Peptides from the Brain and Its Failure in Cerebral Amyloid Angiopathy and Alzheimer's Disease," Brain Pathology 18 (Apr. 2008) 253-266.
Brief PubMed search for metal ions in Alzheimers.
An Office Action dated Sep. 27, 2016, which issued during the prosecution of U.S. Appl. No. 14/926,705.
U.S. Appl. No. 62/642,663, filed Mar. 14, 2018.
An International Search Report and a Written Opinion both dated Aug. 7, 2008, which issued during the prosecution of Applicant's PCT/IL2007/000865.
An Office Action dated Mar. 29, 2013, which issued during the prosecution of U.S. Appl. No. 12/373,306.
An Office Action dated Oct. 31, 2011, which issued during the prosecution of U.S. Appl. No. 12/373,306.
An Office Action dated Oct. 1, 2012, which issued during the prosecution of U.S. Appl. No. 12/373,306.
Notice of Allowance dated Jul. 24, 2013, which issued during the prosecution of U.S. Appl. No. 12/373,306.
An Office Action dated Apr. 11, 2013, which issued during the prosecution of U.S. Appl. No. 13/663,757.
Notice of Allowance dated Oct. 28, 2013, which issued during the prosecution of U.S. Appl. No. 13/663,757.
Elixmann IM et al., "In-vitro evaluation of a drainage catheter with integrated bioimpedance electrodes to determine ventricular size," Biomed Tech 2013; 58 (Suppl. 1) Sep. 2013 (2 pages total).

An Office Action dated Aug. 31, 2015, which issued during the prosecution of U.S. Appl. No. 13/872,794.
An Applicant Initiated Interview Summary dated Dec. 14, 2015, which issued during the prosecution of U.S. Appl. No. 13/872,794.
An Office Action dated Feb. 3, 2016, which issued during the prosecution of U.S. Appl. No. 13/872,794.
Notice of Allowance dated Dec. 9, 2016, which issued during the prosecution of U.S. Appl. No. 14/794,739.
An Applicant Initiated Interview Summary dated Feb. 25, 2016, which issued during the prosecution of U.S. Appl. No. 13/872,794.
An Office Action dated Jun. 15, 2016, which issued during the prosecution of U.S. Appl. No. 13/872,794.
An International Search Report and a Written Opinion both dated Oct. 20, 2016, which issued during the prosecution of Applicant's PCT/IL2016/050728.
An Office Action dated Sep. 21, 2016, which issued during the prosecution of U.S. Appl. No. 14/794,739.
An International Search Report and a Written Opinion both dated Jan. 26, 2017, which issued during the prosecution of Applicant's PCT/IL2016/051161.
Notice of Allowance dated Jul. 14, 2017, which issued during the prosecution of U.S. Appl. No. 13/872,794.
An Office Action dated May 26, 2017, which issued during the prosecution of U.S. Appl. No. 15/453,290.
An International Preliminary Report on Patentability dated Apr. 7, 2009, which issued during the prosecution of Applicant's PCT/IL2007/000865.
Loutzenhiser, "Membrane Potential measurements in renal afferent and efferent arterioles: actions of Angiotensin II", AJP—Renal Physiol Aug. 1, 1997 vol. 273 No. 2 F307-F314.
U.S. Appl. No. 60/830,717, filed Jul. 12, 2006.
Dao-Sheng Liu et al., "Activation of Na+ and K+ Pumping Modes of (Na,K)-ATPase by an Oscillating Electric Field," The Journal of Biological Chemistry, vol. 265. No. 13, May 5, 1990. (pp. 7260-7267).
Robert F. Service.. "Electric fields deliver drugs into tumors." http://news.sciencemaa.ora. Feb. 4, 2015. (5 Pages Total).
Vernengo J, "Injectable Bioadhesive Hydrogels for Nucleus Pulposus Replacement and Repair of the Damaged Intervertebral Disc: A Thesis," Drexel University (Jan. 2007).
Urban JPG et al., "The nucleus of the intervertebral disc from development to degeneration," American Zoologist 40(1): 53-61 (2000).
Cheung KMC et al., "Intervertebral disc regeneration by use of autologous mesenchymal stem cells, an experimental model in rabbits," Abstract from the SRS 2004 Annual Meeting.
Freemont TJ et al., "Degeneration of intervertebral discs: current understanding of cellular and molecular events, and implications for novel therapies," Expert Reviews in Molecular Biology, Mar. 29, 2001 (Cambridge University Press).
An Office Action dated Sep. 12, 2011, which issued during the prosecution of U.S. Appl. No. 12/373,306.
An Office Action dated Jul. 24, 2017, which issued during the prosecution of U.S. Appl. No. 14/982,187.
An International Search Report and a Written Opinion both dated Mar. 10, 2017, which issued during the prosecution of Applicant's PCT/IL2016/051363.
An Office Action dated Apr. 25, 2018, which issued during the prosecution of U.S. Appl. No. 15/637,330.
U.S. Appl. No. 62/444,939, filed Jan. 11, 2017.
An Office Action dated Jul. 10, 2019, which issued during the prosecution of U.S. Appl. No. 15/864,065.
An International Search Report and a Written Opinion both dated May 23, 2019, which issued during the prosecution of Applicant's PCT/IL2019/050284.
An Office Action dated Mar. 25, 2019, which issued during the prosecution of U.S. Appl. No. 15/742,245.
Borlase NM, "The thalamus in Parkinson's Disease," Department of Psychology, University of Canterbury, 2012.
Fernandes J, "Protein May Prevent Neuron Death in Huntington's Patients, Study Finds," huntingtonsdiseasenews.com, Jan. 19, 2017.

(56) References Cited

OTHER PUBLICATIONS

Lee H-J, "Extracellular asynuclein a novel and crucial factor in Lewy body diseases," Nat. Rev. Neurol. 10, 92-98 (Feb. 2014); published online Jan. 28, 2014.
Starr PA et al., "Parkinson's Disease FAQ—Deep Brain Stimulation for Parkinson's Disease," UCSF Apr. 19, 2017.
Perez RG et al., "A Role for Alpha-Synuclein in the Regulation of Dopamine Biosynthesis," The Journal of Neuroscience, Apr. 15, 2002, 22(8):3090-3099.
Breydo L et al., "α-Synuclein misfolding and Parkinson's disease," Biochimica et Biophysica Acta 1822 (2012) 261-285 (Available online Oct. 12, 2011).
Deleidi M et al., "Protein Clearance Mechanisms of Alpha-Synuclein and Amyloid-Beta in Lewy Body Disorders," International Journal of Alzheimer's Disease, vol. 2012.
Xie L et al., "Sleep Drives Metabolite Clearance from the Adult Brain," Science. Oct. 18, 2013; 342(6156).
Valdinocci D et al., "Potential Modes of Intercellular α-Synuclein Transmission," International Journal of Molecular Sciences, Feb. 22, 2017.
U.S. Appl. No. 62/500,747, filed May 3, 2017.
An Office Action dated Jul. 29, 2019, which issued during the prosecution of U.S. Appl. No. 15/618,325.
Sawyer, P N et al. "Measurement of streaming potentials of mammalian blood vessels, aorta and vena cava, in vivo." Biophysical journal vol. 6,5 (1966): 641-51. doi:10.1016/50006-3495(66)86683-3, https://www.ncbi.nlm.nih.gov/pmc/articles/PMC1368020/, viewed on Jul. 22, 2019.
An Office Action dated Nov. 29, 2019, which issued during the prosecution of U.S. Appl. No. 15/969,411.
An Office Action dated Jan. 7, 2020, which issued during the prosecution of U.S. Appl. No. 15/618,325.
An Office Action dated Jan. 7, 2020, which issued during the prosecution of European Patent Application No. 16741703.9.
An Office Action dated Jan. 22, 2020, which issued during the prosecution of U.S. Appl. No. 15/771,551.
An Office Action dated Mar. 6, 2020, which issued during the prosecution of U.S. Appl. No. 15/618,325.
An Office Action together with the English Translation dated Aug. 19, 2020, which issued during the prosecution of Japanese Patent Application No. 2018-521586.
An Office Action dated Mar. 30, 2020, which issued during the prosecution of U.S. Appl. No. 16/574,772.
An Office Action dated Nov. 20, 2020, which issued during the prosecution of U.S. Appl. No. 16/353,407.
An International Search Report and a Written Opinion both dated Dec. 20, 2020, which issued during the prosecution of Applicant's PCT/IL2020/051022.
An Office Action dated Nov. 4, 2021, which issued during the prosecution of U.S. Appl. No. 16/713,660.
An Office Action dated Nov. 15, 2021, which issued during the prosecution of U.S. Appl. No. 16/692,528.
A Notice of Allowance dated Apr. 27, 2022, which issued during the prosecution of U.S. Appl. No. 17/667,051.
A Non-Final Office Action issued in U.S. Appl. No. 17/828,109, dated Apr. 12, 2023.
Austin SA, Santhanam AV, Hinton DJ, Choi DS, Katusic ZS. Endothelial nitric oxide deficiency promotes Alzheimer's disease pathology. J Neurochem. Dec. 2013;127(5):691-700. doi: 10.1111/jnc.12334. Epub Jun. 27, 2013. PMID: 23745722; PMCID: PMC3825764.
Baker TS, Robeny J, Cruz D, Bruhat A, Iloreta AM, Costa A, Oxley TJ. Stimulating the Facial Nerve to Treat Ischemic Stroke: A Systematic Review. Front Neurol. Nov. 18, 2021;12:753182.
Benussi A, Cantoni V, Cotelli MS, Cotelli M, Brattini C, Datta A, Thomas C, Santarnecchi E, Pascual-Leone A, Borroni B. Exposure to gamma tACS in Alzheimer's disease: A randomized, double-blind, sham-controlled, crossover, pilot study. Brain Stimul. May-Jun. 2021;14(3):531-540. doi: 10.1016/j.brs.2021.03.007. Epub Mar. 21, 2021. PMID: 33762220.

Chen J, Wang Z, Chen Q, Fu Y, Zheng K. Transcranial Direct Current Stimulation Enhances Cognitive Function in Patients with Mild Cognitive Impairment and Early/Mid Alzheimer's Disease: A Systematic Review and Meta-Analysis. Brain Sci. Apr. 27, 2022;12(5):562.
Dhaynaut M, Sprugnoli G, Cappon D, Macone J, Sanchez JS, Normandin MD, Guehl NJ, Koch G, Paciorek R, Connor A, Press D, Johnson K, Pascual-Leone A, El Fakhri G, Santarnecchi E. Impact of 40 Hz Transcranial Alternating Current Stimulation on Cerebral Tau Burden in Patients with Alzheimer's Disease: A Case Series. J Alzheimers Dis. 2022;85(4):1667-1676. doi: 10.3233/JAD-215072. PMID: 34958021; PMCID: PMC9023125.
Grossman N, Bono D, Dedic N, Kodandaramaiah SB, Rudenko A, Suk HJ, Cassara AM, Neufeld E, Kuster N, Tsai LH, Pascual-Leone A, Boyden ES. Noninvasive Deep Brain Stimulation via Temporally Interfering Electric Fields. Cell. Jun. 1, 2017;169(6):1029-1041.e16.
Iaccarino HF, Singer AC, Martorell AJ, Rudenko A, Gao F, Gillingham TZ, Mathys H, Seo J, Kritskiy O, Abdurrob F, Adaikkan C, Canter RG, Rueda R, Brown EN, Boyden ES, Tsai LH. Gamma frequency entrainment attenuates amyloid load and modifies microglia. Nature. Dec. 7, 2016;540(7632):230-235. doi: 10.1038/nature20587. Erratum in: Nature. Oct. 2018;562(7725):E1. PMID: 27929004; PMCID: PMC5656389.
Iturria-Medina, Y., Sotero, R., Toussaint, P et al. Early role of vascular dysregulation on late-onset Alzheimer's disease based on multifactorial data-driven analysis. Nat Commun 7, 11934 (2016).
Jamali S, Ross B. Sustained changes in somatosensory gamma responses after brief vibrotactile stimulation. Neuroreport. May 7, 2014;25(7):537-41.
Khedr EM, Salama RH, Abdel Hameed M, Abo Elfetoh N, Seif P. Therapeutic Role of Transcranial Direct Current Stimulation in Alzheimer Disease Patients: Double-Blind, Placebo-Controlled Clinical Trial. Neurorehabil Neural Repair. May 2019;33(5):384-394.
Levi H, Schoknecht K, Prager O, Chassidim Y, Weissberg I, Serlin Y, Friedman A. Stimulation of the sphenopalatine ganglion induces reperfusion and blood-brain barrier protection in the photothrombotic stroke model. PLoS One. 2012;7(6):e39636. doi: 10.1371/journal.pone.0039636. Epub Jun. 22, 2012. PMID: 22745798; PMCID: PMC3382129.
Liu Y, Liu S, Tang C, Tang K, Liu D, Chen M, Mao Z, Xia X. Transcranial alternating current stimulation combined with sound stimulation improves cognitive function in patients with Alzheimer's disease: Study protocol for a randomized controlled trial. Front Aging Neurosci. Jan. 9, 2023;14:1068175.
Liu Y, Tang C, Wei K, Liu D, Tang K, Chen M, Xia X, Mao Z. Transcranial alternating current stimulation combined with sound stimulation improves the cognitive function of patients with Alzheimer's disease: A case report and literature review. Front Neurol. Sep. 23, 2022;13:962684.
Luo Y, Yang H, Yan X, Wu Y, Wei G, Wu X, Tian X, Xiong Y, Wu G, Wen H. Transcranial Direct Current Stimulation Alleviates Neurovascular Unit Dysfunction in Mice With Preclinical Alzheimer's Disease. Front Aging Neurosci. Apr. 14, 2022;14:857415.
Manippa V, Palmisano A, Nitsche MA, Filardi M, Vilella D, Logroscino G, Rivolta D. Cognitive and Neuropathophysiological Outcomes of Gamma-tACS in Dementia: A Systematic Review. Neuropsychol Rev. Mar. 6, 2023. doi: 10.1007/s11065-023-09589-0. Epub ahead of print.
Martorell AJ, Paulson AL, Suk HJ, Abdurrob F, Drummond GT, Guan W, Young JZ, Kim DN, Kritskiy O, Barker SJ, Mangena V, Prince SM, Brown EN, Chung K, Boyden ES, Singer AC, Tsai LH. Multi-sensory Gamma Stimulation Ameliorates Alzheimer's-Associated Pathology and Improves Cognition. Cell. Apr. 4, 2019;177(2):256-271.e22.
McDermott B, Porter E, Hughes D, McGinley B, Lang M, O'Halloran M, Jones M. Gamma Band Neural Stimulation in Humans and the Promise of a New Modality to Prevent and Treat Alzheimer's Disease. J Alzheimers Dis. 2018;65(2):363-392.
Saver JL, Kharaishvili N, Janelidze T, Beridze M, Zarqua N, Solberg Y, Bornstein NM; IMPACT-24M Trial Investigators. Refined

(56) References Cited

OTHER PUBLICATIONS

Sphenopalatine Ganglion Stimulator Placement and Intensity Setting to Augment Blood Flow and Neurologic Function. Stroke. Dec. 2019;50(12):3512-3518.

Suk HJ, Buie N, Xu G, Banerjee A, Boyden ES, Tsai LH. Vibrotactile stimulation at gamma frequency mitigates pathology related to neurodegeneration and improves motor function. Front Aging Neurosci. May 18, 2023;15:1129510.

Talman WT, Nitschke Dragon D. Neuronal nitric oxide mediates cerebral vasodilatation during acute hypertension. Brain Res. Mar. 30, 2007;1139:126-32. doi: 10.1016/j.brainres.2007.01.008. Epub Jan. 8, 2007.

Wu L, Cao T, Li S, Yuan Y, Zhang W, Huang L, Cai C, Fan L, Li L, Wang J, Liu T, Wang J. Long-term gamma transcranial alternating current stimulation improves the memory function of mice with Alzheimer's disease. Front Aging Neurosci. Sep. 15, 2022;14:980636.

Sangjun Lee, "Individually customized transcranial temporal interference stimulation for focused modulation of deep brain structures: a simulation study with different head models", Scientific Reports, 2020, vol. 10, No. 11730 (11 pages total).

United States Office Action issued Dec. 6, 2023 in U.S. Appl. No. 18/351,247.

"Sphenopalatine Ganglion (SPG) Block (Injection Technique)," DFW Pain Institute, PLLC DBA NorTex Spine & Joint Institute, https://www.nortexspineandjoint.com/sphenopalatine-ganglion-block/, Reviewed Jan. 30, 2023.

\* cited by examiner

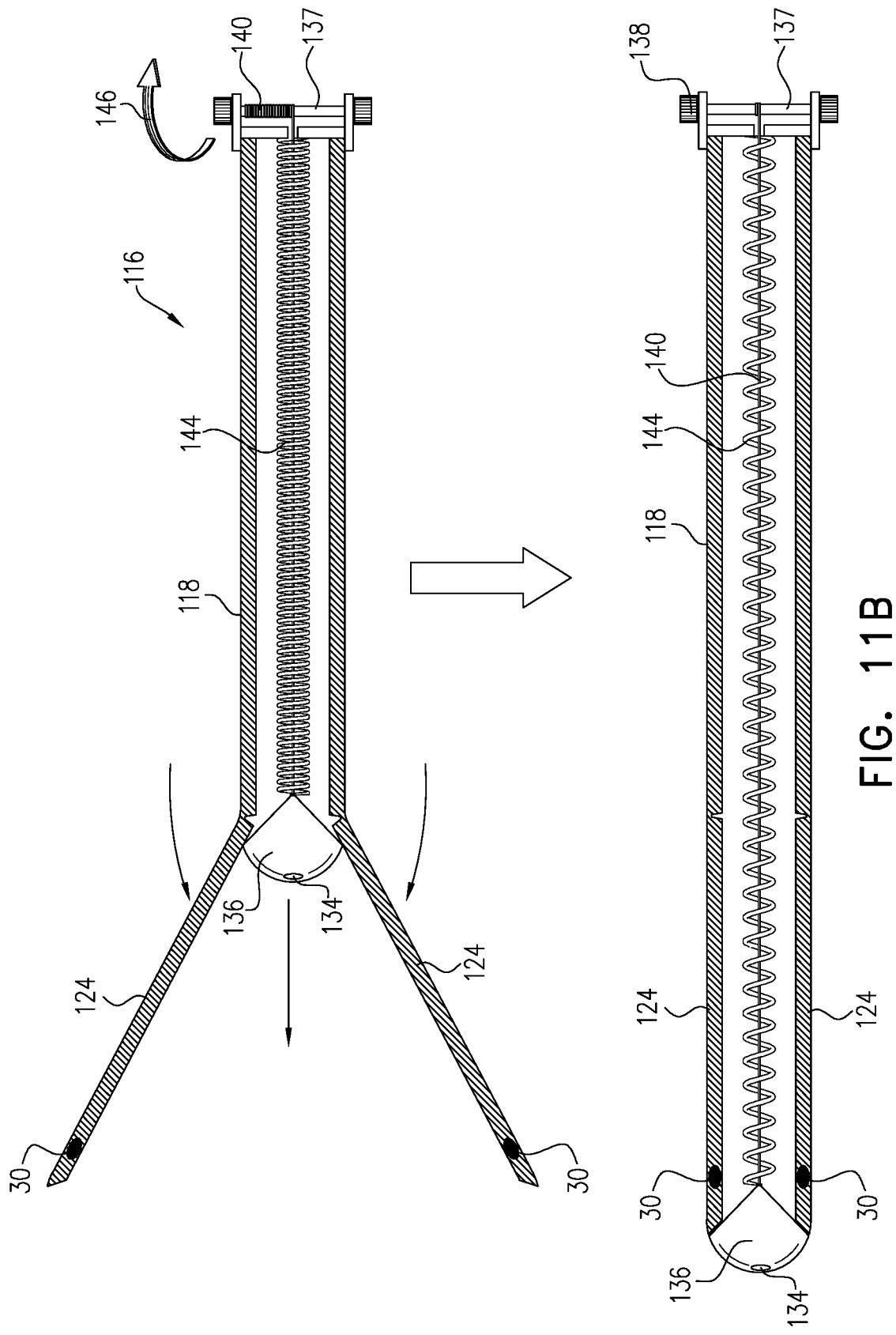

BLOOD FLOW ENHANCEMENT THERAPY SYSTEM

FIELD OF THE INVENTION

The present application relates generally to enhancing cerebral blood flow, and specifically to stimulation of the sphenopalatine ganglion (SPG).

BACKGROUND

International Patent Application WO 2001/085094 to Shalev et al. describes apparatus for modifying a property of a brain of a patient, including one or more electrodes, adapted to be applied to a site selected from a group of sites consisting of: a sphenopalatine ganglion (SPG) of the patient and a neural tract originating in or leading to the SPG. A control unit is adapted to drive the one or more electrodes to apply a current to the site capable of inducing an increase in permeability of a blood-brain barrier (BBB) of the patient, (b) a change in cerebral blood flow of the patient, and/or (c) an inhibition of parasympathetic activity of the SPG. Other embodiments are also described.

U.S. Pat. No. 9,233,245 to Lamensdorf et al. describes a method for treating a subject, including applying electrical stimulation to a site of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve. The stimulation is configured to excite nervous tissue of the site at a strength sufficient to induce at least one neuroprotective occurrence selected from the group consisting of: an increase in cerebral blood flow (CBF) of the subject, and a release of one or more neuroprotective substances, and insufficient to induce a significant increase in permeability of a blood-brain barrier (BBB) of the subject. Other embodiments are also described.

SUMMARY OF THE INVENTION

In accordance with some applications of the present invention, a system and method are provided for increasing cerebral blood flow (CBF) of a patient in cardiac arrest or in an acute post-cardiac arrest phase. For some applications two or more electrodes are coupled to tissue of a patient in cardiac arrest or in an acute post-cardiac arrest phase and CBF of the patient is increased by activating a power source to drive the electrodes to apply current to a sphenopalatine ganglion (SPG) of the patient. For some applications, the SPG stimulation is applied after a defibrillator is used to apply an electric charge to a heart of the patient.

For some applications, an SPG stimulating device is placed in a nose of the patient for nasal-only stimulation of the SPG. The SPG stimulation device typically has a sheath, a nasal stabilizer disposed around the sheath for stabilizing the device with respect to a nostril of the patient, an electrode mount slidably disposed within the sheath, and at least one electrode coupled to the mount and deployable out of the sheath (e.g., by pushing the electrode mount distally or by pulling the sheath proximally) in order to position the electrode to stimulate the SPG. The SPG stimulating device may include a camera configured to facilitate navigation of the sheath toward the SPG, and/or a sensor configured to sense a physiological response of the patient to stimulation of the SPG.

Alternatively, for some applications, the electrodes of the SPG stimulating device are not deployed from within a sheath, but rather a distal end portion of a housing of the SPG stimulating device is shaped to define a plurality of electrode arms that are configured to open outward away from a central longitudinal axis of the housing during deployment of the electrode arms. At least one electrode is coupled to each electrode arm such that when the distal end portion is placed within the nose and the electrode arm is deployed, the at least one electrode is positioned to stimulate the SPG.

Alternatively, for some applications, an inflatable SPG stimulating device is a flexible tube configured for placement within the nose and has at least one inflatable electrode mount at a distal end portion of the tube with at least one electrode coupled to the inflatable mount, and an inflation actuator at a proximal end portion of the tube. When the inflatable SPG stimulating device is placed within the nose and the at least one inflatable electrode mount is inflated, the at least one electrode is positioned to stimulate the SPG. Typically, the inflatable SPG stimulating device also includes an inflatable nasal stabilizer configured to stabilize the flexible tube with respect to a nostril of the nose when the flexible tube is disposed within the nose and the inflatable nasal stabilizer is inflated.

There is therefore provided, in accordance with some applications of the present invention, a method for treating a patient in cardiac arrest or in an acute post-cardiac arrest phase, the method including:

coupling two or more electrodes to tissue of the patient in cardiac arrest or in an acute post-cardiac arrest phase; and increasing cerebral blood flow (CBF) of the patient in cardiac arrest or in an acute post-cardiac arrest phase by activating a power source to drive the electrodes to apply current to a sphenopalatine ganglion (SPG) of the patient.

For some applications, coupling the electrodes to the tissue includes positioning the electrodes within a nose of the patient such that the electrodes are in position to stimulate the SPG.

For some applications, coupling the electrodes to the tissue includes positioning the electrodes on skin over a mandibular notch of the patient such that the electrodes are in position to stimulate the SPG.

For some applications, coupling the electrodes to the tissue includes positioning the electrodes against gingiva of the patient such that the electrodes are in position to stimulate the SPG.

For some applications, coupling the electrodes to the tissue includes positioning the electrodes against the hard palate of a mouth of the patient such that the electrodes are in position to stimulate the SPG.

For some applications, coupling the electrodes to the tissue includes coupling the electrodes to the tissue within 24 hours of an onset of the cardiac arrest.

For some applications, coupling the electrodes to the tissue includes coupling the electrodes to the tissue within 6 hours of an onset of the cardiac arrest.

For some applications:

the method further includes activating a defibrillator to apply an electric charge to a heart of the patient, and activating the power source to drive the electrodes to apply current to the SPG of the patient includes activating the power source to drive the electrodes to apply current to the SPG after the activation of the defibrillator.

For some applications, activating the power source to drive the electrodes to apply current to the SPG after the activation of the defibrillator includes activating the power source to drive the electrodes to apply current to the SPG within 1 hour after the activation of the defibrillator.

There is further provided, in accordance with some applications of the present invention, a medical device including:
  a defibrillator configured to apply an electric charge to a heart of a patient;
  a sphenopalatine ganglion (SPG) stimulating device for stimulating an SPG of the patient via two or more electrodes configured to be coupled to tissue of the patient; and
  circuitry configured to drive the defibrillator and the SPG stimulating device such that when the circuitry is activated, the circuitry drives the defibrillator to apply an electric charge to the heart and thereafter drives the electrodes to apply current to the SPG of the patient.

There is further provided, in accordance with some applications of the present invention, a sphenopalatine ganglion (SPG) stimulating device for stimulating an SPG of a patient, the device including:
  a sheath having a proximal end portion and a distal end portion, the distal end portion shaped to define at least one electrode opening;
  a nasal stabilizer disposed around the sheath and configured to stabilize the sheath with respect to a nostril of a nose of the patient when the sheath is disposed within the nose;
  an electrode mount, slidably disposed within the sheath; and
  at least one electrode coupled to the electrode mount and deployable out of the sheath through the at least one electrode opening to position the at least one electrode to stimulate the SPG.

For some applications, the sheath is flexible.

For some applications, the sheath includes silicone.

For some applications, a distance between the nasal stabilizer and the at least one electrode opening is 4-8 cm.

For some applications, an outer diameter of the nasal stabilizer is 3-15 mm greater than an outer diameter of the sheath.

For some applications, an outer diameter of the sheath is 3-8 mm.

For some applications, the device further includes a releasable pre-deployment lock, configured to prevent sliding of the electrode mount within the sheath.

For some applications, the at least one electrode is configured to curve away from a central longitudinal axis of the sheath during deployment of the at least one electrode.

For some applications, the nasal stabilizer is connected to the sheath.

For some applications, the nasal stabilizer is inseparable from the sheath without breaking a portion of the device.

For some applications, the at least one electrode includes a plurality of electrodes.

For some applications, the plurality of electrodes includes exactly three independently-addressable electrodes.

For some applications, the electrode mount further includes a plurality of flexible prongs, and each of the plurality of electrodes is coupled to a respective one of the flexible prongs.

For some applications, the at least one electrode is arranged such that distal motion of the electrode mount with respect to the sheath deploys the at least one electrode out of the sheath through the at least one electrode opening.

For some applications, the nasal stabilizer is arranged to remain in a same location with respect to the sheath during the distal motion of the electrode mount with respect to the sheath.

For some applications, the device further includes a releasable post-deployment lock, configured to prevent sliding of the electrode mount within the sheath following the distal motion of the electrode mount with respect to the sheath.

For some applications, the at least one electrode is arranged such that proximal motion of the sheath with respect to the electrode mount deploys the at least one electrode out of the sheath through the at least one electrode opening.

For some applications, the sheath is arranged to slide proximally with respect to the nasal stabilizer during the proximal motion of the sheath with respect to the electrode mount.

For some applications, the sheath is shaped to define a longitudinal slit on a lateral side of the sheath, and the nasal stabilizer is connected to the electrode mount through the longitudinal slit.

For some applications, the longitudinal slit extends from a distal end of the sheath to a location along the sheath that is proximal to the nasal stabilizer.

For some applications, the longitudinal slit extends from the distal end of the sheath to a proximal end of the sheath.

For some applications, the device further includes an implant handle for stabilizing the electrode mount during the proximal motion of the sheath, the implant handle protruding from the electrode mount through the longitudinal slit at a location along the electrode mount that is proximal to the nasal stabilizer.

For some applications, the device further includes an insulating coating that coats the at least one electrode, the insulating coating leaving at least one exposed region of the at least one electrode configured for driving current into tissue of the patient.

For some applications, the insulating coating leaves a plurality of exposed regions of the at least one electrode for driving current into tissue of the patient.

For some applications, the device further includes a sensor coupled to the sheath and configured to sense a physiological response of the patient to stimulation of the SPG.

For some applications, the sensor is a Doppler flowmetry sensor.

For some applications, the sensor is fixed to the sheath.

For some applications, the device further includes a sensor coupled to the electrode mount and configured to sense a physiological response of the patient to stimulation of the SPG.

For some applications, the sensor is fixed to a lateral side of the electrode mount.

For some applications, the sheath is shaped to define at least one sensor hole, and the sensor fixed to the electrode mount is configured to sense the physiological response of the patient through the sensor hole.

For some applications, the sensor is a Doppler flowmetry sensor.

For some applications, the device further includes a camera coupled to the sheath and configured to facilitate navigation of the sheath toward the SPG.

For some applications, the camera is fixed to the sheath.

For some applications, the device further includes a camera fixed to a distal end of the electrode mount, configured to facilitate navigation of the distal end of the electrode mount toward the SPG.

For some applications, the device further includes a control unit including a battery and circuitry and configured to drive the at least one electrode to stimulate the SPG.

For some applications, the control unit is wearable.

For some applications, the device further includes a mandibular notch electrode coupled to the control unit and couplable to skin over a mandibular notch of the patient, and the control unit is configured to drive the at least one electrode to stimulate the SPG by driving a current between the at least one electrode and the mandibular notch electrode.

For some applications, the device further includes a gingival electrode frame and a gingival electrode mounted on the gingival frame, the gingival electrode coupled to the control unit and couplable, using the gingival electrode frame, to gingiva of the patient, and the control unit is configured to drive the at least one electrode to stimulate the SPG by driving a current between the at least one electrode and the gingival electrode.

For some applications, the device further includes a dental arch electrode frame configured to be mounted to a dental arch of the patient and at least one greater palatine foramen (GPF) electrode coupled to the dental arch electrode frame, the at least one GPF electrode coupled to the control unit and couplable, using the dental arch electrode frame, to a hard palate of the patient over a GPF of the patient, and the control unit is configured to drive the at least one electrode to stimulate the SPG by driving a current between the at least one electrode and the at least one GPF electrode.

For some applications, the device further includes a greater palatine foramen electrode frame and a greater palatine foramen electrode mounted on the greater palatine foramen electrode frame, the greater palatine foramen electrode coupled to the control unit and couplable, using the greater palatine foramen electrode frame, to tissue over a greater palatine foramen of the patient, and the control unit is configured to drive the at least one electrode to stimulate the SPG by driving a current between the at least one electrode and the greater palatine foramen electrode.

For some applications, the device further includes a sensor configured to sense a physiological response of the patient to stimulation of the SPG and to send to the control unit a signal indicative of the physiological response.

For some applications, the at least one electrode includes a plurality of electrodes, and the control unit is configured to designate at least one of the plurality of electrodes to exclude from use for stimulating the SPG in response to the signal.

For some applications, the sensor is a Doppler flowmetry sensor.

For some applications, the Doppler flowmetry sensor is configured to be coupled to skin of the patient over a carotid artery of the patient.

There is further provided, in accordance with some applications of the present invention, a sphenopalatine ganglion (SPG) stimulating device for stimulating an SPG of a patient, the device including:

a flexible housing having a proximal end portion and a distal end portion, wherein the distal end portion is (a) shaped to define a plurality of electrode arms configured to open outward away from a central longitudinal axis of the housing during deployment of the electrode arms, each electrode arm coupled to the flexible housing at a proximal end of the electrode arm, and (b) configured to be placed within a nose of a patient;

a deployment actuator configured to actuate the deployment of the electrode arms;

a camera (a) disposed at the distal end portion of the housing prior to the deployment of the electrode arms, wherein proximal motion of the camera toward the proximal end portion of the housing is associated with the deployment of the electrode arms, and (b) configured to facilitate navigation of the housing toward the SPG; and for each electrode arm, at least one electrode coupled to the electrode arm such that when the distal end portion is placed within the nose and the electrode arm is deployed, the at least one electrode is positioned to stimulate the SPG.

For some applications, the plurality of electrode arms includes exactly three electrode arms.

There is further provided, in accordance with some applications of the present invention, a sphenopalatine ganglion (SPG) stimulating device for stimulating an SPG of a patient, the device including:

a flexible tube configured for placement within a nose of a patient and having a proximal end portion and a distal end portion, (a) the distal end portion including at least one inflatable electrode mount, and (b) the proximal end portion including an inflation actuator via which the at least one inflatable electrode mount is inflatable; and at least one electrode coupled to the at least one inflatable electrode mount such that when the device is placed within the nose and the at least one inflatable electrode mount is inflated, the at least one electrode is positioned to stimulate the SPG.

For some applications, the device further includes an inflatable nasal stabilizer disposed around the flexible tube and configured to stabilize the flexible tube with respect to a nostril of the nose when the flexible tube is disposed within the nose and the inflatable nasal stabilizer is inflated.

For some applications, the at least one inflatable electrode mount includes a plurality of inflatable electrode mounts positioned circumferentially around the distal end portion of the flexible tube, and the at least one electrode includes a respective at least one electrode coupled to each of the plurality of inflatable electrode mounts.

For some applications, the plurality of inflatable electrode mounts includes exactly three inflatable electrode mounts.

For some applications, the at least one inflatable electrode mount includes an inflatable electrode balloon, and the at least one electrode includes a plurality of electrodes positioned circumferentially around the inflatable balloon such that when the device is placed within the nose and the inflatable electrode balloon is inflated, at least one of the plurality of electrodes is positioned to stimulate the SPG.

The present invention will be more fully understood from the following detailed description of applications thereof, taken together with the drawings, in which:

BRIEF DESCRIPTION OF THE DRAWINGS

FIGS. 11A-B are schematic illustrations of a nasal SPG stimulating device, in accordance with some applications of the present invention;

DETAILED DESCRIPTION

Figure 1:
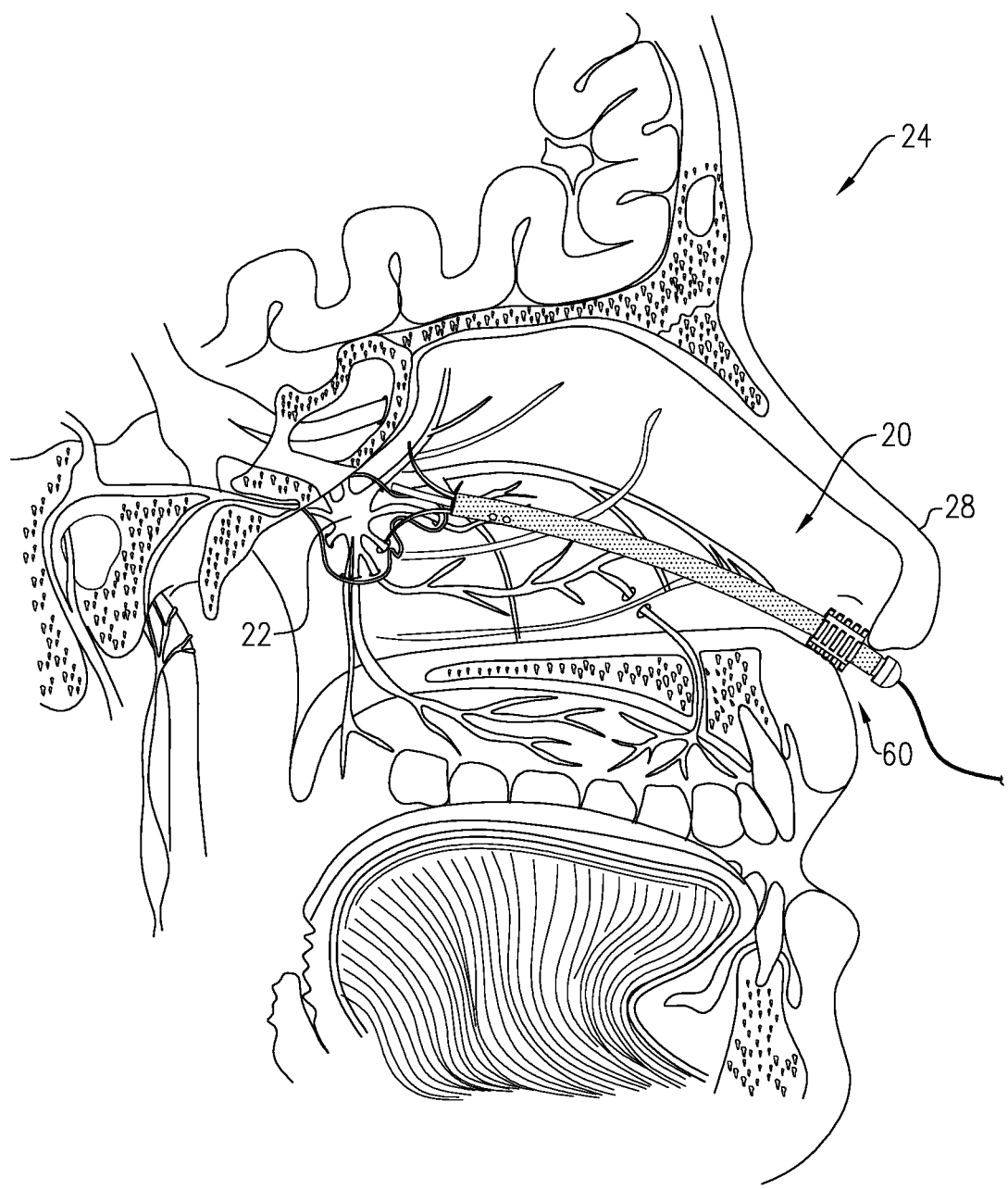
FIG. 1 is a schematic illustration of an SPG stimulating device for stimulating an SPG of a patient, in accordance with some applications of the present invention.

Reference is now made to FIG. 1, which is a schematic illustration of an SPG stimulating device 20 for stimulating an SPG 22 of a patient 24, in accordance with some applications of the present invention. For some applications, stimulating SPG 22 may be used as a method for treating a patient in cardiac arrest or in an acute post-cardiac arrest phase. The method for treatment typically includes coupling two or more electrodes to tissue of patient 24 in cardiac arrest or in an acute post-cardiac arrest phase, and increasing cerebral blood flow (CBF) of patient 24 by activating a power source (such as battery 96 inside control unit 26 shown in FIGS. 4A-B) to drive the electrodes to apply current to SPG 22 of patient 24. It is noted that the two or more electrodes may be, for example, any of the electrode embodiments described herein, as well as any electrodes described with respect to other stimulating devices configured to stimulate the SPG of a patient (e.g., as described in U.S. Ser. No. 18/229,379 to Gross et al., which is incorporated herein by reference). For some applications, the electrodes are coupled to the tissue of patient 24 within 24 hours, e.g., within 6 hours, of an onset of the cardiac arrest.

For clarity of illustration, SPG stimulation is generally shown and described with respect to a single SPG 22. In any of the configurations described herein, the SPG stimulation may be applied to either a single SPG (the left or the right SPG) or both SPGs, in which case many of the elements of the system are duplicated for the left and right sides of the head.

Figure 3:
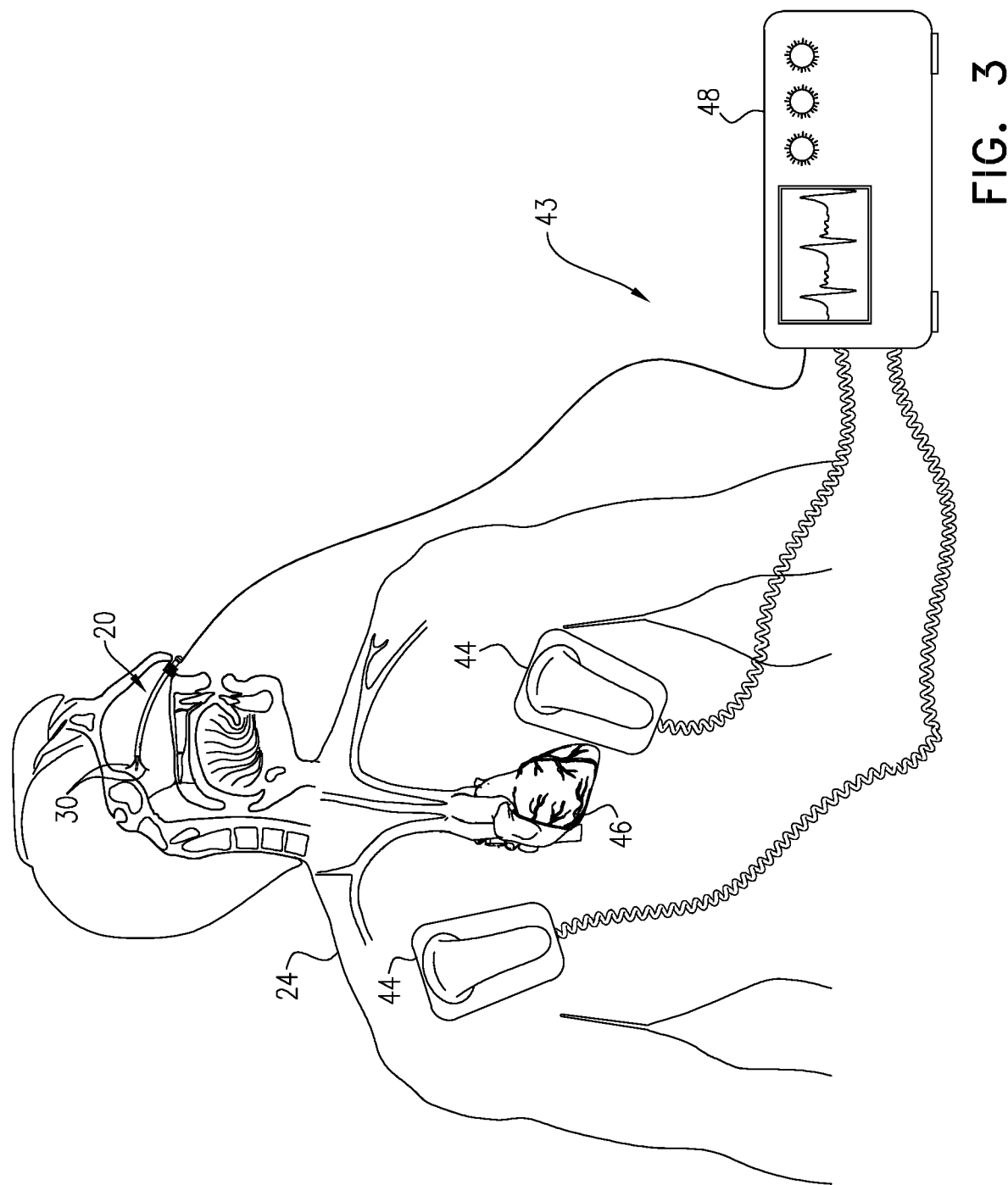
FIG. 3 is a schematic illustration of a combination of a defibrillator and an SPG stimulating device, in accordance with some applications of the present invention.

For some applications, such as is shown for example in FIGS. 1, 3, and 4, the tissue is within a nose 28 of patient 24, and coupling the electrodes to the tissue is done by positioning the electrodes within nose 28 of patient 24 such that the electrodes are in position to stimulate SPG 22 of patient 24. It is noted that positioning the electrodes within nose 28 may be done using electrodes 30 of any of the nasal SPG stimulating devices 20 described herein.

Figure 2:
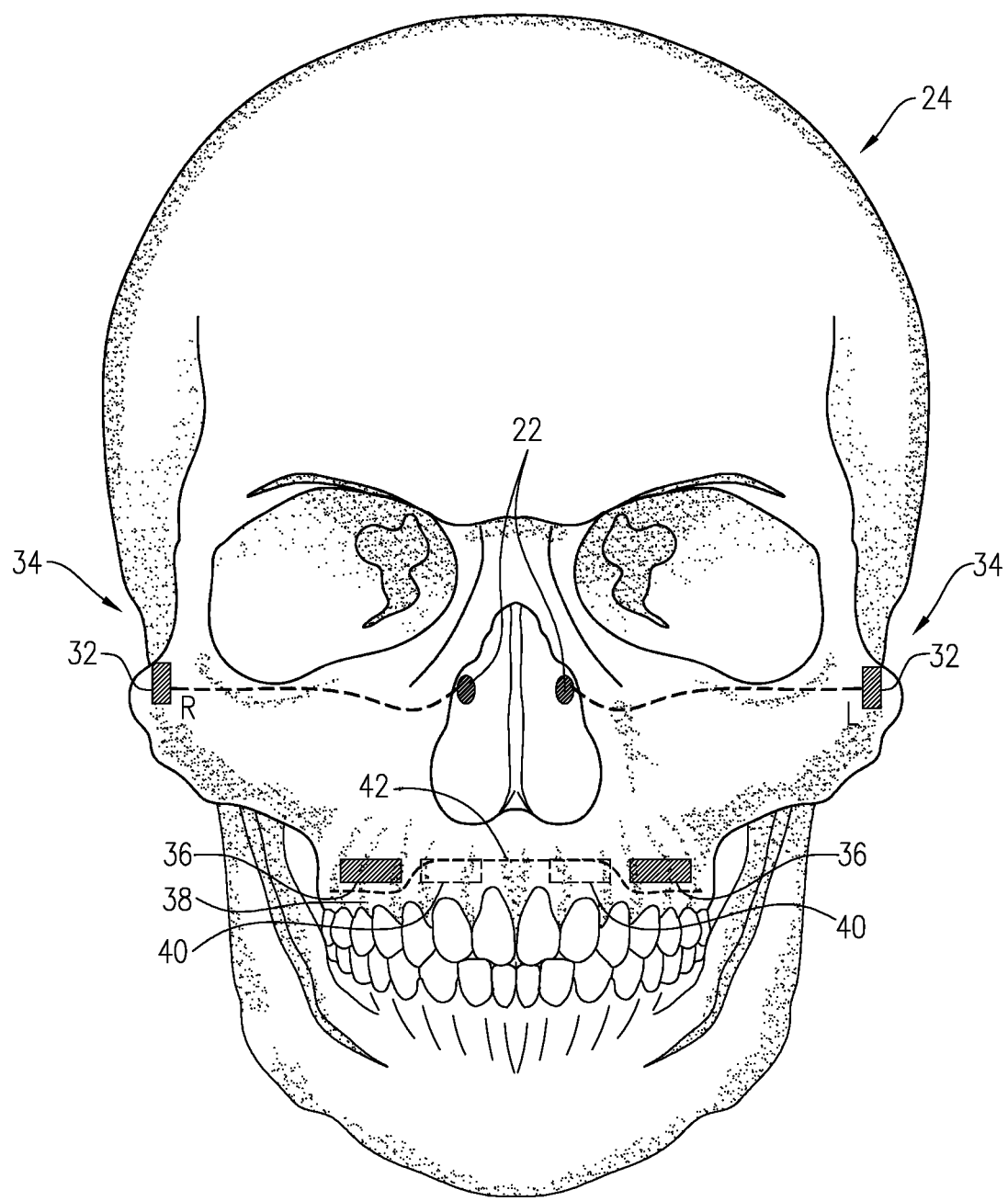
FIG. 2 illustrates non-nasal sites for stimulating the SPG of the patient, in accordance with some applications of the present invention.

Reference is now made to FIG. 2, which illustrates non-nasal sites for stimulating SPG 22 of patient 24, in accordance with some applications of the present invention. For some applications, coupling the electrodes to the tissue comprises positioning mandibular notch electrodes 32 on skin over a mandibular notch 34 of patient 24 (such as is shown in FIG. 8B) such that electrodes 32 are in position to stimulate SPG 22. Alternatively or additionally, coupling the electrodes to the tissue comprises positioning gingival electrodes 36 against gingiva 38 of patient 24 (such as is shown in FIGS. 9B-C) such that electrodes 36 are in position to stimulate SPG 22. Alternatively or additionally, coupling the electrodes to the tissue comprises positioning greater palatine foramen (GPF) electrodes 40 against a hard palate 42 (such as is shown in FIG. 10B) of a mouth of patient 24 such that electrodes 40 are in position to stimulate SPG 22.

Figure 4B:
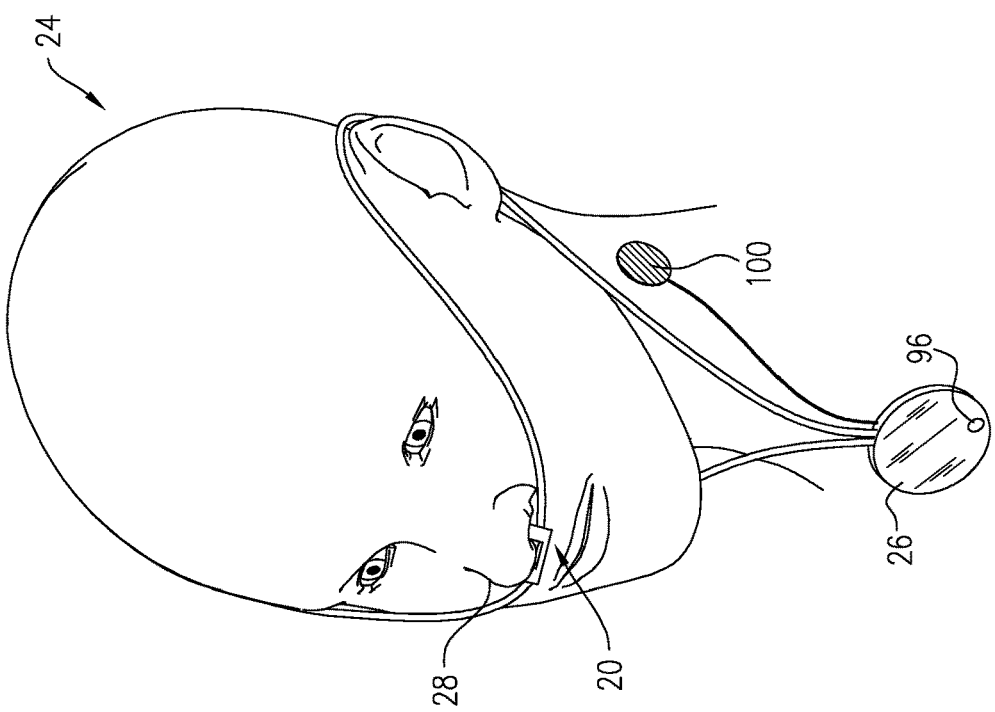
FIGS. 4A-B show the SPG stimulating device placed within a nose of a patient and connected to a control unit, in accordance with some applications of the present invention.
Figure 4A:
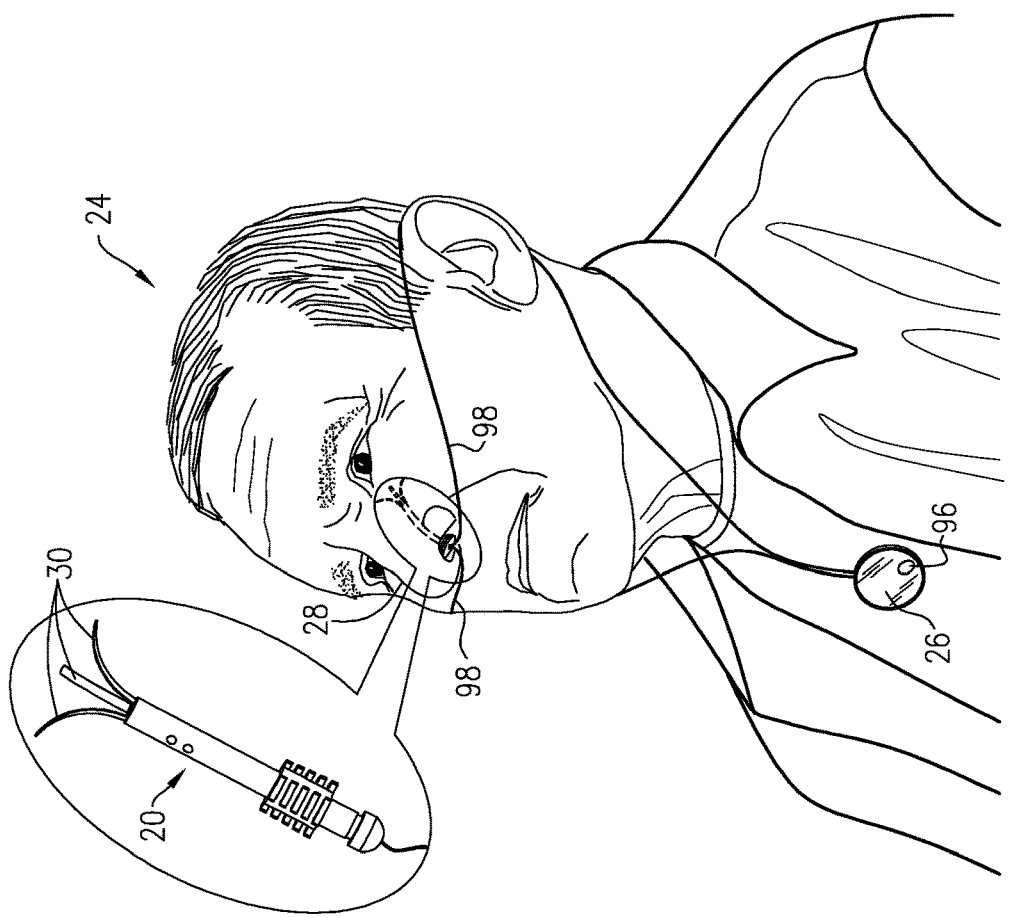

Reference is now made to FIG. 3, which is a schematic illustration of a combination of a defibrillator and SPG stimulating device, in accordance with some applications of the present invention. For some applications, the method of treatment of patient 24 in cardiac arrest or in an acute post-cardiac arrest phase further includes activating a defibrillator 44 to apply an electric charge to a heart 46 of patient 24. Typically, defibrillator 44 is activated to apply the electric charge to heart 46 and the power source (e.g., circuitry 48 as shown in FIG. 3, or battery 96 in control unit 26 as shown in FIGS. 4A-B) is activated to drive the electrodes (e.g., electrodes 30, electrodes 32, electrodes 36, electrodes 40, and/or electrodes 160) to apply current to SPG 22 after the activation of defibrillator 44, e.g., within 1 hour after the activation of defibrillator 44. (For some applications, the current is applied to SPG 22 shortly before activation of defibrillator 44.)

For some applications, a medical device 43 may be used that comprises a defibrillator and an SPG stimulator, for example as shown in FIG. 3. Medical device 43 includes defibrillator 44 configured to apply an electric charge to heart 46 of patient 24, SPG stimulating device 20 for stimulating an SPG of patient 24 via two or more electrodes 30, and circuitry 48 configured to drive defibrillator 44 and SPG stimulating device 20 such that when circuitry 48 is activated, circuitry 48 drives defibrillator 44 to apply an electric charge to heart 46 and thereafter drives the electrodes to apply current to SPG 22 of patient 24. It is noted that circuitry 48 for driving defibrillator 44 and SPG stimulating device 20 may be all in one housing (such as is shown in FIG. 3), or respective parts of circuitry 48 for driving defibrillator 44 and SPG stimulating device 20, respectively, may be in separate housings. It is noted that SPG stimulating device 20 is shown as a nasal SPG stimulating device in FIG. 3 by way of example only (any of the embodiments described herein for an SPG stimulating device may be used, as well as any other electrodes or stimulating device configured to stimulate the SPG of a patient). It is also noted that while FIG. 3 shows medical device 43 comprising a defibrillator and SPG stimulating device, the method of first activating a defibrillator to apply an electric charge to the heart of the patient and thereafter applying stimulation to the SPG of the patient may be performed using separate defibrillator and SPG stimulating devices.

For some applications, alternatively or additionally to increasing CBF to treat a patient in cardiac arrest or in an acute post-cardiac arrest phase, SPG stimulating device 20 may be used for any of the following:

patients who have had an ischemic stroke-either pre/during/post a thrombectomy or for patients who are not eligible for thrombectomy, patients who have vasospasm, e.g., post subarachnoid hemorrhage, stroke rehabilitation,
prevention and treatment of post-surgery cognitive decline,
treatment of vascular dementia,
treatment post transient ischemic attack (TIA),
treatment of Alzheimer's disease,
stroke prevention post transcatheter aortic valve implantation (TAVI), or
increasing permeability of the Blood Brain Barrier (BBB)

Reference is now made to FIGS. 4A-B, which show SPG stimulating device 20 placed within nose 28 of patient 24 and connected to a control unit 26 (further described hereinbelow), in accordance with some applications of the present invention. It is noted that SPG stimulating device 20 shown in FIGS. 4A-B may be any of the variations of SPG stimulating device 20 described hereinbelow.

Reference is now made to FIGS. 5A-C and 6A-B, which are schematic illustrations of different variations of a nasal SPG stimulating device 20, in accordance with some applications of the present invention. For some applications, SPG stimulating device 20 includes the following:
  a sheath 50 having a proximal end portion 52 and a distal end portion 54, distal end portion 54 shaped to define at least one electrode opening 56 (shown in FIG. 5B and FIG. 6B);
  a nasal stabilizer 58 disposed around sheath 50 and configured to stabilize sheath 50 with respect to a nostril 60 (shown in FIG. 1) of nose 28 of patient 24 when sheath 50 is disposed within nose 28 (such as is shown in FIGS. 4A-B);
  an electrode mount 62, slidably disposed within sheath 50; and
  at least one electrode 30 coupled to electrode mount 62 and deployable out of sheath 50 through at least one electrode opening 56 to position at least one electrode 30 to stimulate SPG 22.

Typically, sheath 50 is flexible. For example, sheath 50 may be made of a flexible polymer, e.g., silicone. For some applications, dimensions of SPG stimulating device 20 may include one or more of the following:
  a distance D1 (shown in FIGS. 5A and 6A) between nasal stabilizer 58 and at least one electrode opening 56 is at least 4 cm and/or less than 8 cm,
  an outer diameter D2 (shown in FIGS. 5A and 6A) of sheath 50 is at least 3 mm and/or less than 8 mm, and
  an outer diameter D3 (shown in FIGS. 5A and 7B) of nasal stabilizer 58 is at least 3 mm and/or less than 15 mm.

Figure 5A:
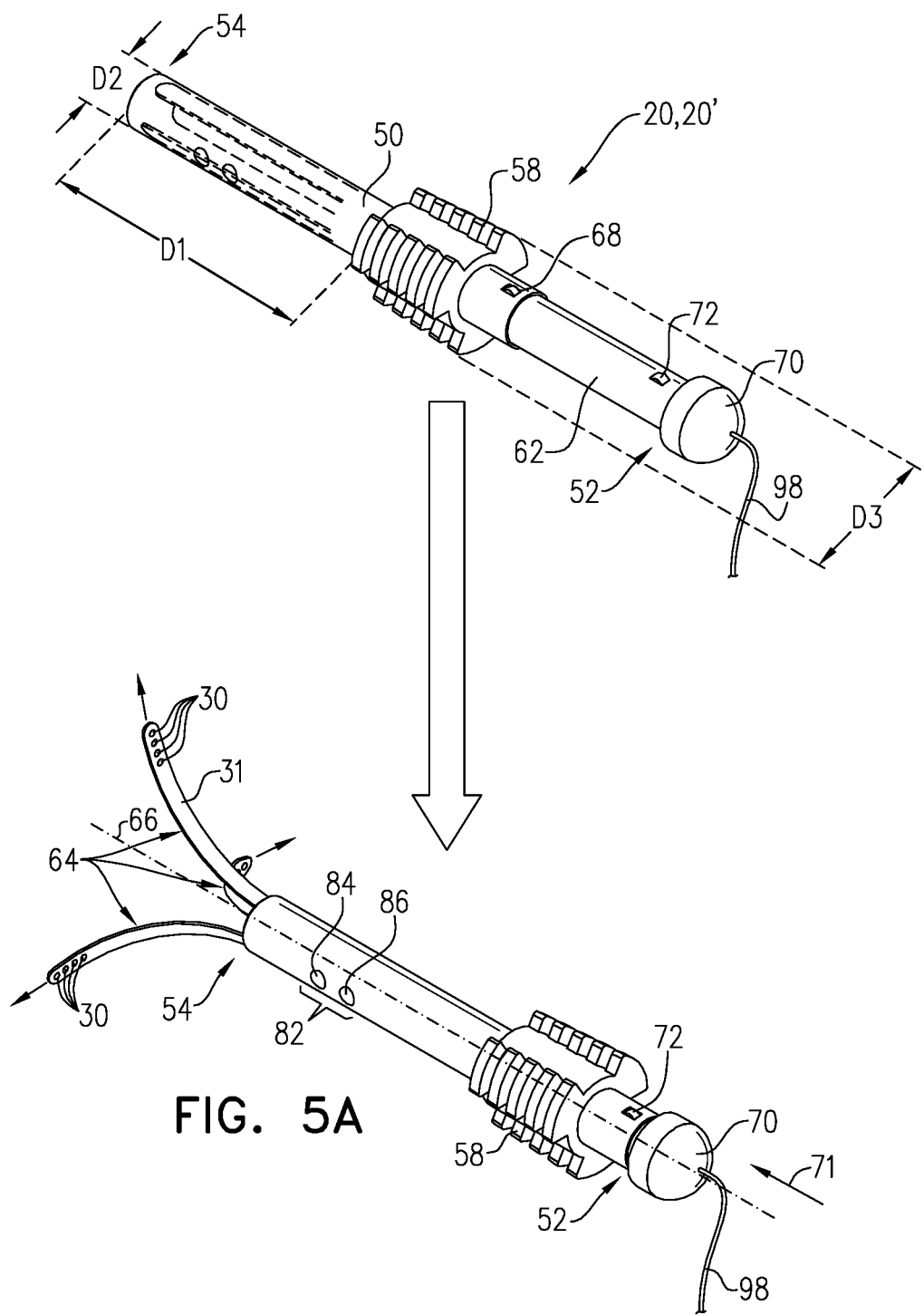
FIGS. 5A-C and 6A-B are schematic illustrations of different variations of a nasal SPG stimulating device, in accordance with some applications of the present invention.

For some applications, SPG stimulating device 20 has a plurality of electrodes 30, e.g., exactly three independently-addressable electrodes 30. For some applications, electrode mount 62 has a plurality of flexible prongs 64, with each of the plurality of electrodes 30 coupled to a respective one of flexible prongs 64. During deployment of electrode(s) 30, electrode(s) 30 may curve away from a central longitudinal axis 66 of sheath 50, e.g., electrode prong(s) 64 to which electrode(s) 30 are coupled may curve away from central longitudinal axis 66 during deployment of electrode(s) 30 out of sheath 50 (such as is shown in FIG. 5A). For some applications, such as is shown in FIG. 5A, a plurality of electrodes 30, e.g., gold plated nitinol electrodes, are coupled to each electrode prong 64. Alternatively, for some applications, such as is shown in FIG. 6B, a single electrode 30, e.g., gold plated nitinol electrode, is coupled to each electrode prong 64.

For some applications, an insulating coating 31 coats electrode(s) 30, the insulating coating leaving at least one exposed region, e.g., a plurality of exposed regions, of electrode(s) 30 configured for driving current into tissue of patient 24. For example, a traditional electrode lead may be used comprising platinum-iridium electrodes that are placed along an insulating lead and are all connected to an inner conductive wire of the lead.

For some applications, SPG stimulating device 20 includes a releasable pre-deployment lock 68 that prevents electrode mount 62 from sliding within sheath 50. This allows SPG stimulating device 20 to be positioned within nose 28 of patient 24 without the medical practitioner needing to worry about electrode mount 62 sliding within sheath 50. Once SPG stimulating device 20 is correctly positioned within nose 28, the medical practitioner can unlock releasable pre-deployment lock 68 and slidably deploy electrode(s) 30, as further described hereinbelow. Releasable pre-deployment lock 68 may be any of kind of lock that holds electrode mount 62 stationary with respect to sheath 50 and can be released to enable electrode mount 62 to slide with respect to sheath 50. For example, releasable pre-deployment lock 68 may include a small hole in sheath 50 and a depressible protrusion on electrode mount 62 configured to protrude from electrode mount 62 in the absence of an external force pushing the protrusion down; in a locked state the protrusion protrudes through the hole in sheath 50 and can be depressed so as to enable electrode mount 62 to slide.

Figure 5B:
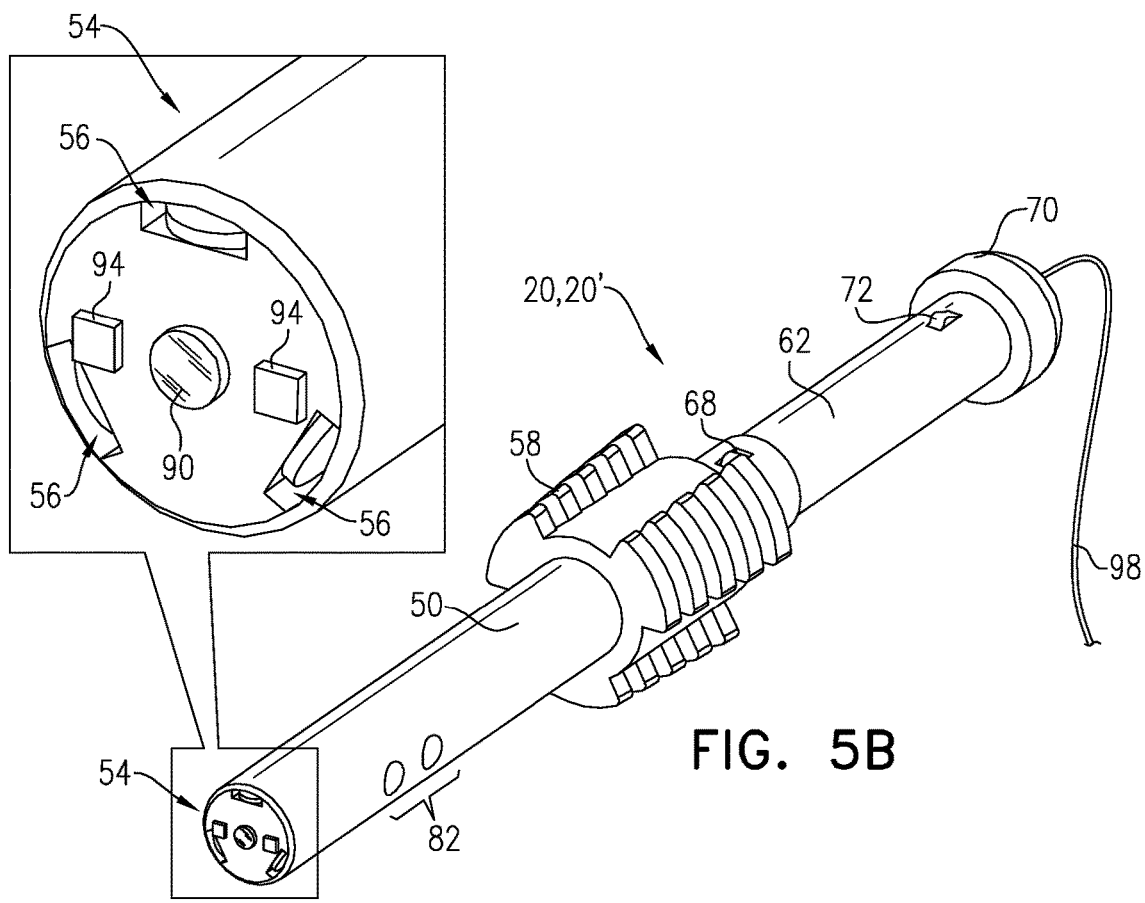
Figure 5C:
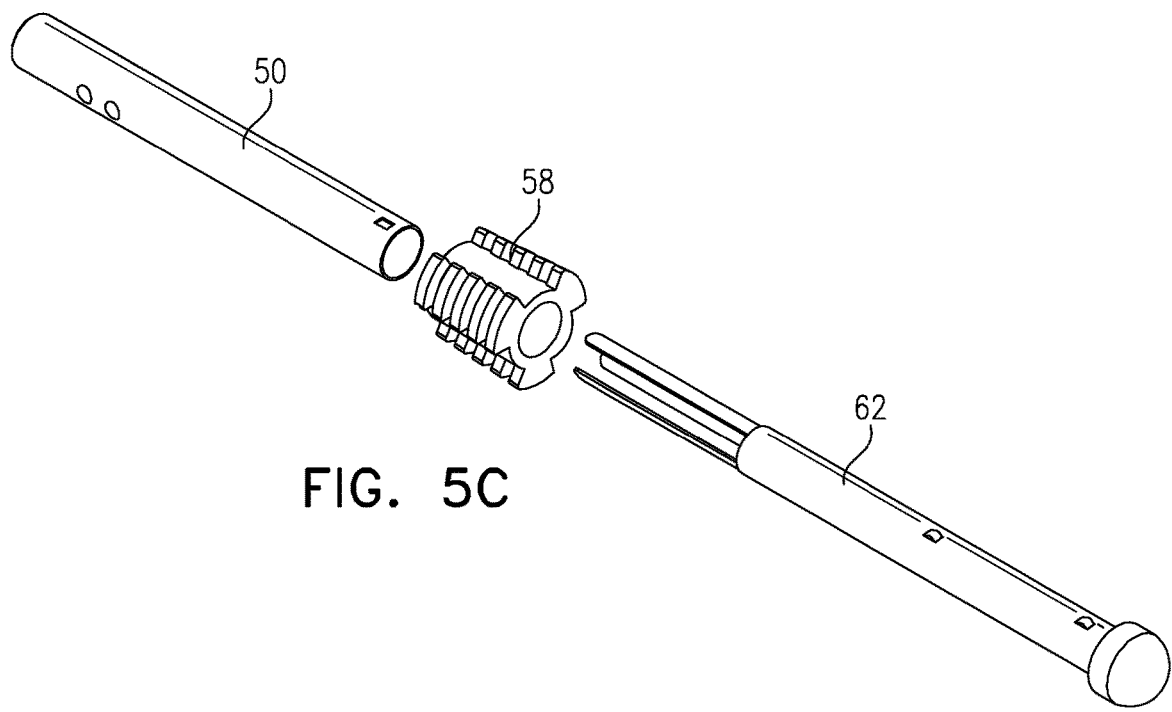

Reference is now made specifically to FIGS. 5A-C, which depict a SPG stimulating device 20', which is an implementation of SPG stimulating device 20. Electrode(s) 30 of SPG stimulating device 20' are arranged such that distal motion of electrode mount 62 with respect to sheath 50 deploys electrode(s) 30 out of sheath 50 through electrode opening(s) 56. After the medical practitioner has positioned SPG stimulating device 20' within nose 28 of patient 24, the medical practitioner pushes on a proximal end 70 of electrode mount 62 in order to slide electrode mount 62 distally with respect to sheath 50. FIG. 5A depicts the distal motion (represented by arrow 71) of electrode mount 62 with respect to sheath 50. Nasal stabilizer 58 is arranged to remain in a same location with respect to sheath 50 during the distal motion of electrode mount 62 with respect to sheath 50. For some applications, nasal stabilizer 58 is connected to sheath 50, e.g., nasal stabilizer 58 may be inseparable from sheath 50 without breaking a portion of the device or is otherwise not intended to be separated from sheath 50 during a medical procedure. For illustrative purposes, FIG. 5C shows an exploded view of sheath 50, nasal stabilizer 58, and electrode mount 62.

For some applications, SPG stimulating device 20' further includes a releasable post-deployment lock 72 configured to prevent sliding of electrode mount 62 within sheath 50 following the distal motion of electrode mount 62 with respect to sheath 50. This prevents electrode(s) 30 from moving within nose 28 of patient 24 once they have been deployed and are in position to stimulate SPG 22 of patient 24. Releasable post-deployment lock 72 may be the same type of lock as releasable pre-deployment lock 68 or may be a different type of lock. In order to remove SPG stimulating device 20' from within nose 28 of patient 24, releasable post-deployment lock 72 is released and electrode mount 62 is pulled proximally by proximal end 70 of electrode mount 62 in order to pull electrode(s) 30 back into sheath 50. Releasable pre-deployment lock 68 is then optionally locked again and SPG stimulating device 20' can be pulled out of nose 28 of patient 24.

Figure 6A:
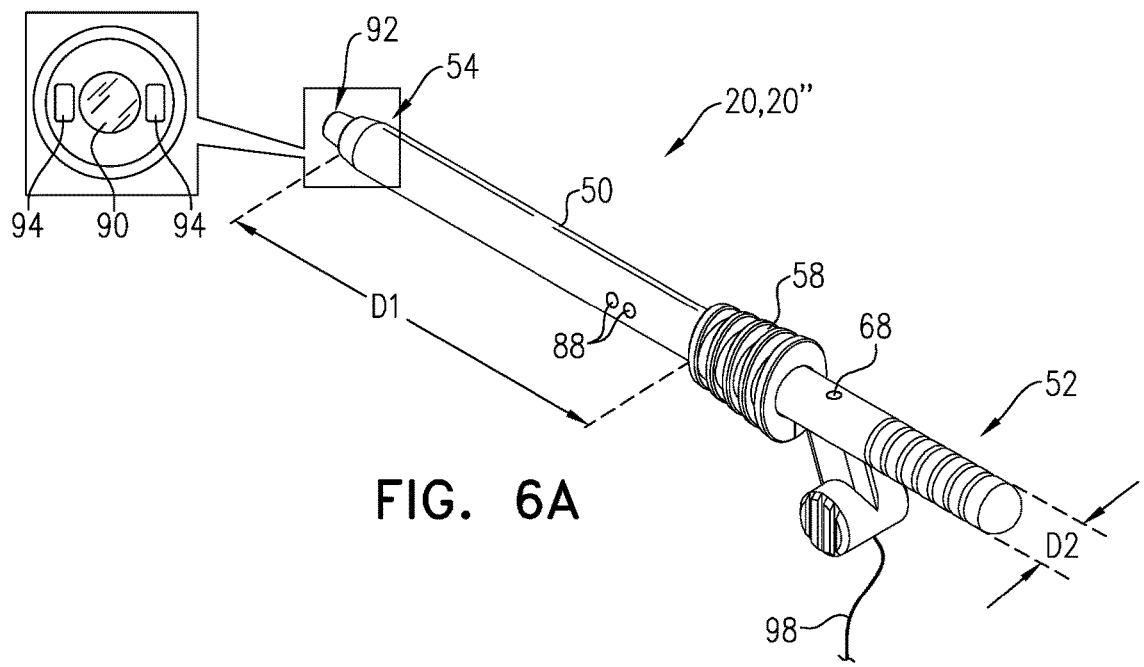
Figure 6B:
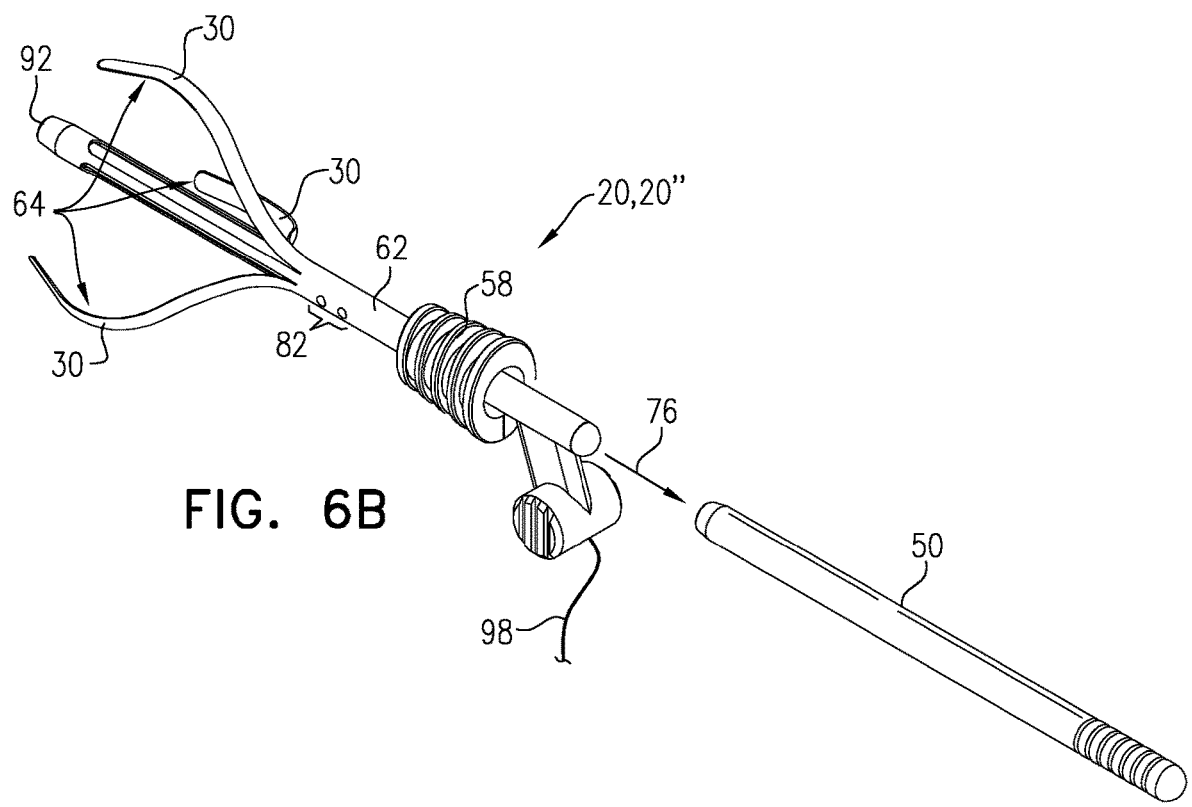

Reference is now made specifically to FIGS. 6A-B, which depict an SPG stimulating device 20", which is an implementation of SPG stimulating device 20, in accordance with some applications of the present invention. Electrode(s) 30 are arranged such that proximal motion of sheath 50 with respect to electrode mount 62 deploys electrode(s) 30 out of sheath 50 through electrode opening 56. After the medical practitioner has positioned SPG stimulating device 20" within nose 28 of patient 24, the medical practitioner releases releasable pre-deployment lock 68 and pulls on proximal end portion 52 of sheath 50 in order to slide sheath 50 proximally off electrode mount 62, as illustrated by arrow 76.

Figure 7A:
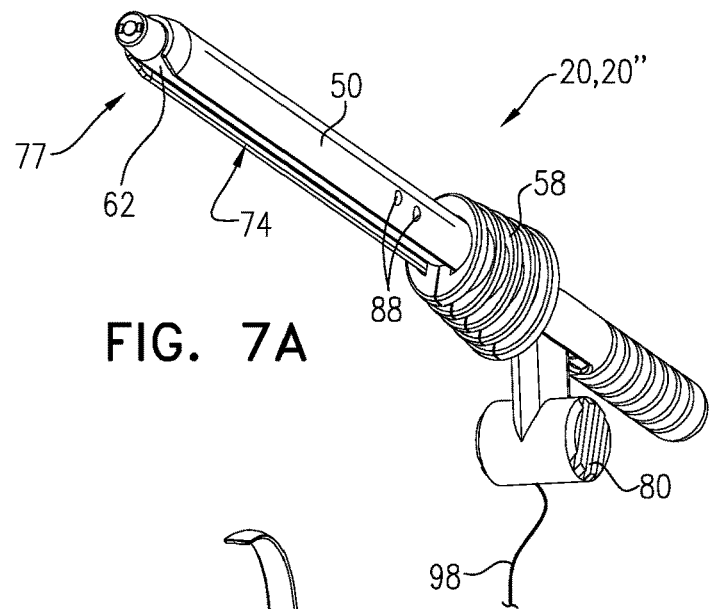
FIGS. 7A-C show various views of the SPG stimulating device of FIGS. 6A-B, in accordance with some applications of the present invention.
Figure 7B:
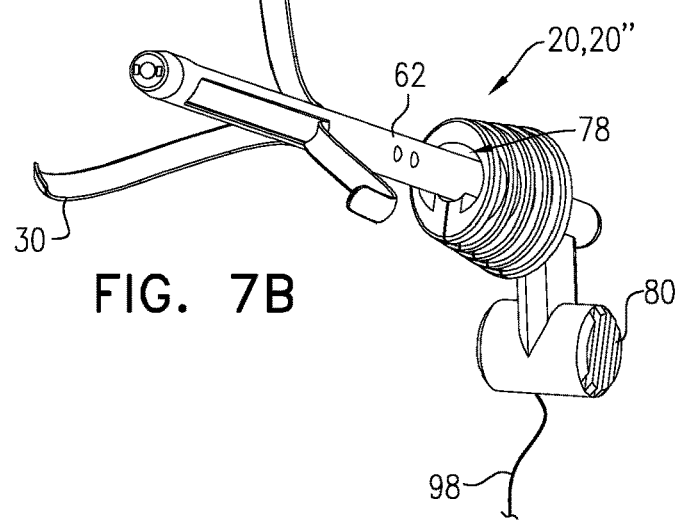
Figure 7C:
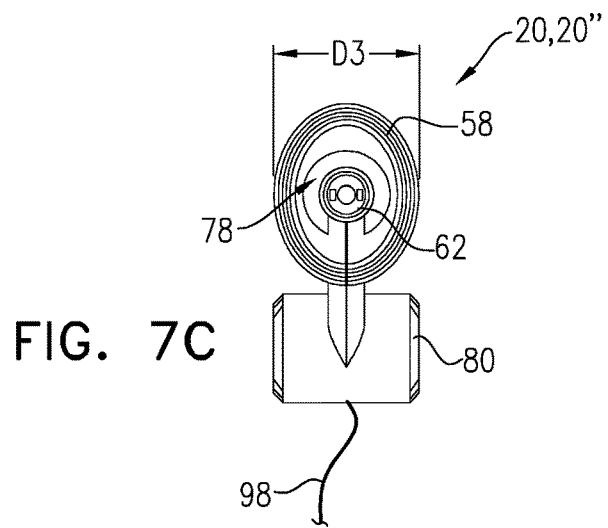

Reference is now made to FIGS. 7A-C, which show various views of SPG stimulating device 20", in accordance with some applications of the present invention. Sheath 50 is arranged to slide proximally with respect to nasal stabilizer 58 during the proximal motion of sheath 50 with respect to electrode mount 62. As illustrated in FIG. 6B, nasal stabilizer 58 remains in place to stabilize SPG stimulating device 20" within nose 28 of patient 24 after sheath 50 has been removed in order to deploy electrode(s) 30. This is achieved by sheath 50 having a longitudinal slit 74 on a lateral side of sheath 50 and nasal stabilizer 58 being connected to electrode mount 62 through the longitudinal slit. As sheath 50 is pulled proximally, the portion of nasal stabilizer 58 that is connected to electrode mount 62 slides through longitudinal slit 74, allowing sheath 50 to be removed. Typically, longitudinal slit 74 extends from a distal end 77 of sheath 50 to a location along sheath 50 that is proximal to nasal stabilizer 58 (such as is shown in FIG. 7A). For some applications, longitudinal slit 74 extends from distal end 77 of sheath 50 to a proximal end of sheath 50 (configuration not shown). For some applications, SPG stimulating device 20" further includes an implant handle 80 for stabilizing electrode mount 62 during the proximal motion of sheath 50. Implant handle 80 protrudes from electrode mount 62 through longitudinal slit 74 at a location along electrode mount 62 that is proximal to nasal stabilizer 58.

FIGS. 7B-C show different perspective views of the connection between nasal stabilizer 58 and electrode mount 62 of SPG stimulating device 20". As further illustrated by FIGS. 7B-C, except at the circumferential location at which nasal stabilizer 58 is connected to electrode mount 62, there is a radial gap 78 between nasal stabilizer 58 and electrode mount 62 that allows the medical practitioner to slide sheath 50 back onto electrode mount 62 in a distal direction in order to reposition electrode(s) 30 within sheath 50. Releasable pre-deployment lock 68 is then optionally locked again, and SPG stimulating device 20" can be pulled out of nose 28 of patient 24.

Reference is again made to FIGS. 5A-C and 6A-B. For some applications, SPG stimulating device 20 includes a sensor 82 configured to sense a physiological response of patient 24 to stimulation of SPG 22. For some applications, sensor 82 is a Doppler flowmetry sensor including a laser light source 84, e.g., fiber-optic laser, and a photodetector 86, e.g., an optical fiber that collects and guides light to a photodetector, to measure light that was emitted by laser light source 84 and reflected back from tissue of patient 24. For some applications, such as for SPG stimulating device 20' shown in FIGS. 5A-C, sensor 82 is coupled to sheath 50, e.g., fixed to sheath 50. Alternatively, for some applications, such as for SPG stimulating device 20" shown in FIGS. 6A-B, sensor 82 is coupled to electrode mount 62, e.g., fixed to a lateral side of electrode mount 62, and sheath 50 is shaped to define at least one sensor hole 88 through which sensor 82 senses the physiological response of patient 24.

Typically, SPG stimulating device 20 includes a camera 90, e.g., a micro camera, or a fiber-optic camera, to facilitate navigation of the device toward SPG 22. For some applications, such as for SPG stimulating device 20' shown in FIGS. 5A-C, camera 90 is coupled to sheath 50, e.g., fixed to sheath 50, at a distal end of sheath 50 (shown in FIG. 5B) and is configured to facilitate navigation of sheath 50 toward SPG 22. Alternatively, for some applications, such as for SPG stimulating device 20" shown in FIGS. 6A-B, camera 90 is fixed to a distal end 92 of electrode mount 62 (shown in FIG. 6A) in order to facilitate navigation of distal end 92 of electrode mount 62 toward SPG 22. Typically, one or more light sources 94 (e.g., LED light sources) are positioned near camera 90 in order to provide illumination for camera 90.

Reference is again made to FIGS. 4A-B. Typically, SPG stimulating device 20 has a control unit 26. Control unit 26 has a battery 96 and is configured to drive electrode(s) 30 to stimulate SPG 22. For some applications, control unit 26 is wearable, e.g., coupled to a body of patient 24 using an adhesive, or worn around the patient's neck on a strap. Electrode(s) 30 of SPG stimulating device 20 are connected to control unit 26 via electrode leads 98 (shown in FIGS. 5A-C, 6A-B, and 7A-C). For some applications, control unit 26 has Bluetooth capabilities allowing control unit 26 to be controlled by a wireless device, such as a tablet or a smart phone, and for data from control unit 26 to be stored in a cloud-based database. Similarly to sensor 82 described hereinabove, for some applications, SPG stimulating device 20 further includes a sensor 100 that is not disposed on SPG stimulating device itself and is configured to sense a physiological response of patient 24 to stimulation of SPG 22 and to send to control unit 26 a signal indicative of the physiological response. For example, sensor 100 may be a Doppler flowmetry sensor, e.g., a Doppler flowmetry sensor coupled to skin of patient 24 over a carotid artery of patient 24 (such as is shown in FIG. 4B). For some applications, SPG stimulating device 20 has a plurality of electrodes 30 and control unit 26 is configured to designate at least one of the plurality of electrodes 30 to exclude from use for stimulating SPG 22 in response to the signal from sensor 100, e.g., in response to determining that the excluded has no desired effect or less of a desired effect on the patient.

Figure 8A:
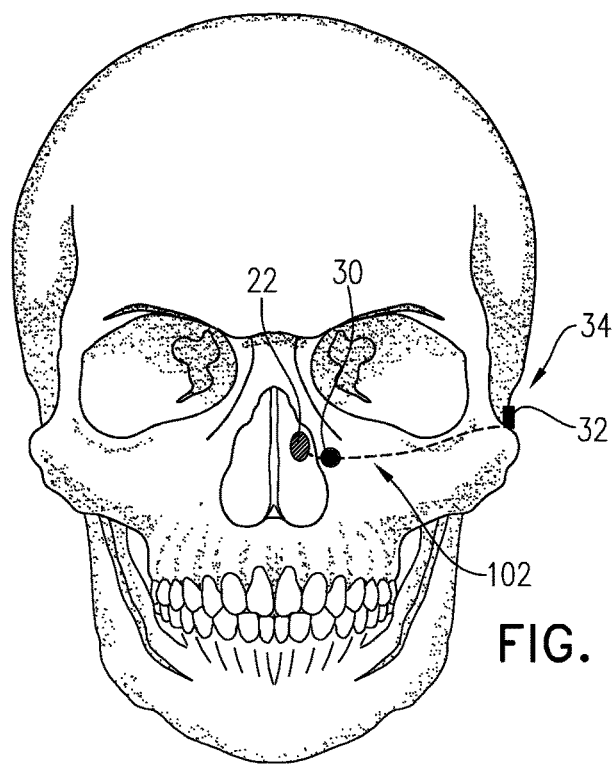
FIGS. 8A-B, 9A-C, and 10A-B show a SPG stimulating device comprising electrodes placed at non-nasal locations, in accordance with some applications of the present invention.
Figure 8B:
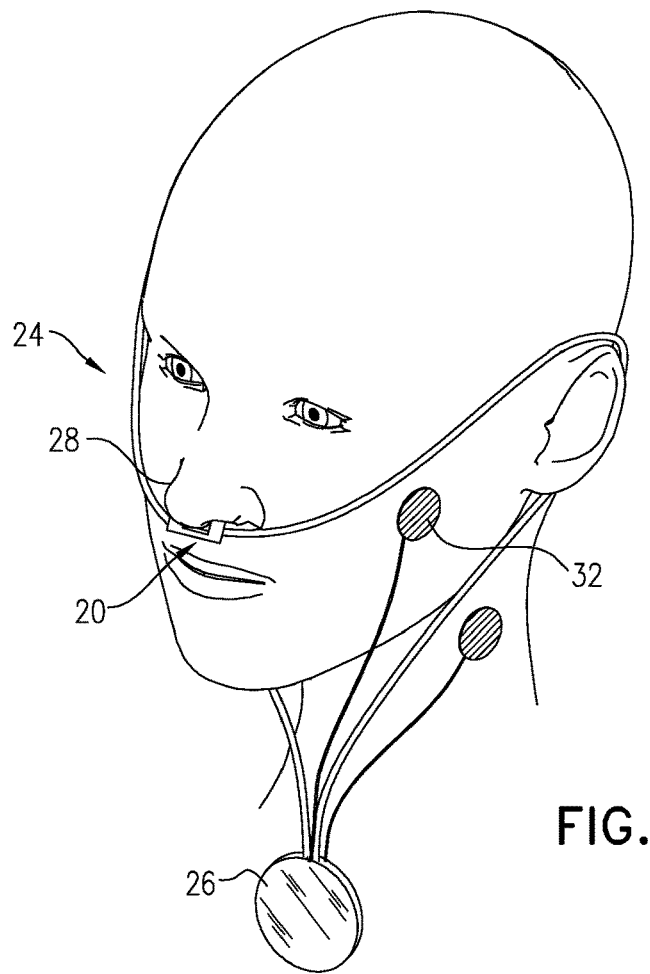
Figure 9C:
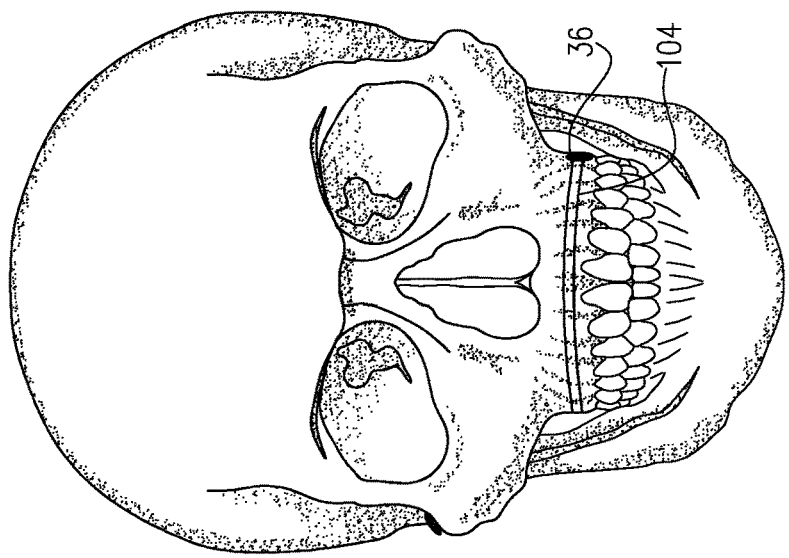
Figure 9B:
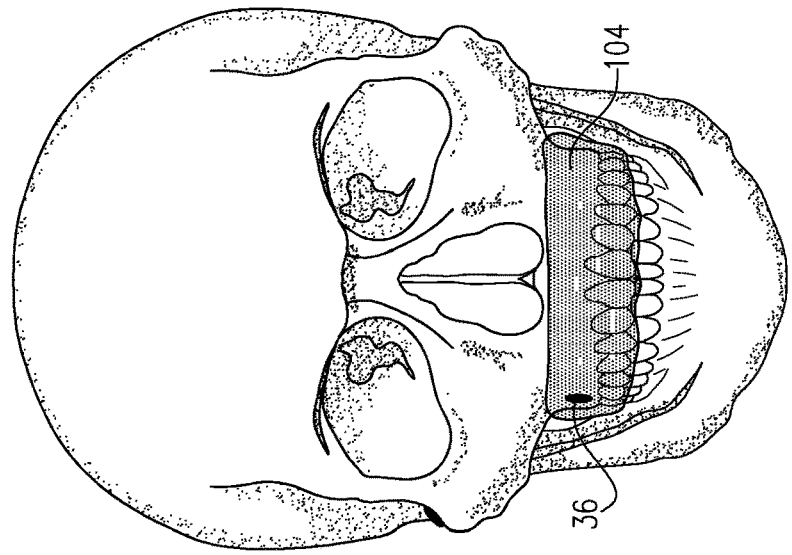

Reference is now made to FIGS. 8A-B, which show SPG stimulating device 20 in combination with at least one mandibular notch electrode 32 coupled to control unit 26 and coupled to skin over mandibular notch 34 of patient 24, in accordance with some applications of the present invention. Control unit 26 drives electrode(s) 30 to stimulate SPG 22 by driving a current between electrode(s) 30 and mandibular notch electrode 32 (as illustrated by dashed current path 102).

Figure 9A:
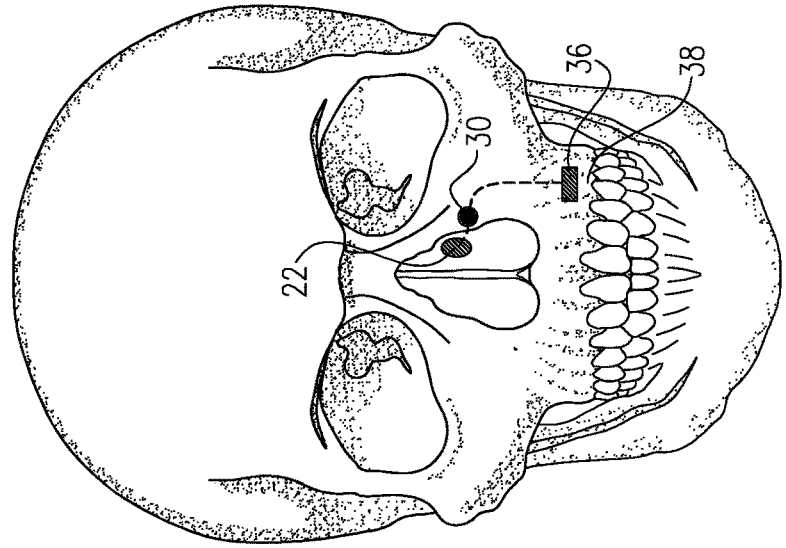

Reference is now made to FIGS. 9A-C, which show SPG stimulating device 20 in combination with at least one gingival electrode 36 mounted on a gingival electrode frame 104, in accordance with some applications of the present invention. Gingival electrode 36 is coupled to control unit 26 and is couplable, using gingival electrode frame 104, to gingiva 38 of patient 24. Control unit 26 drives electrode(s) 30 to stimulate SPG 22 by driving a current between electrode(s) 30 and gingival electrode 36 (as illustrated by dashed current path 106). FIGS. 9B-9C show different examples of gingival electrode frame 104.

Figure 10A:
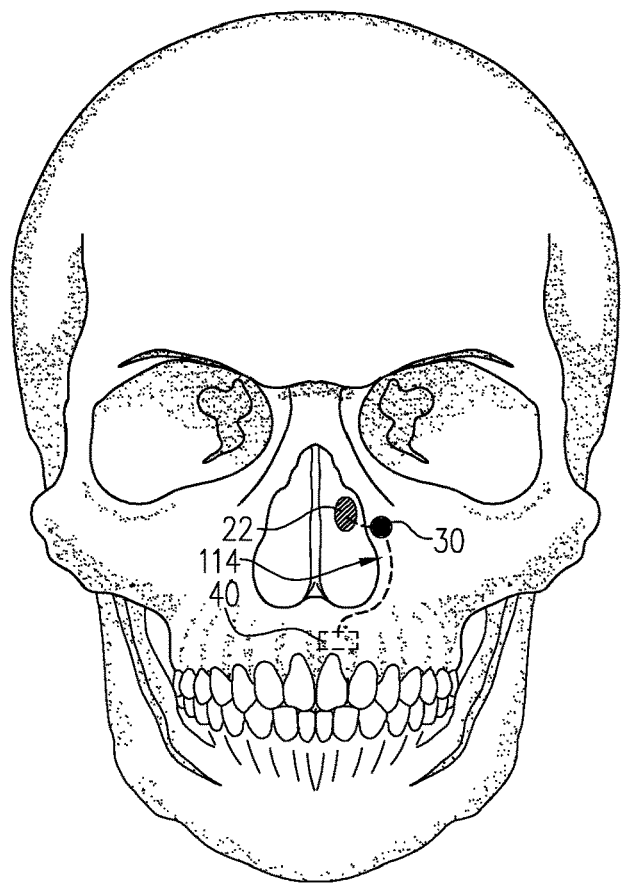
Figure 10B:
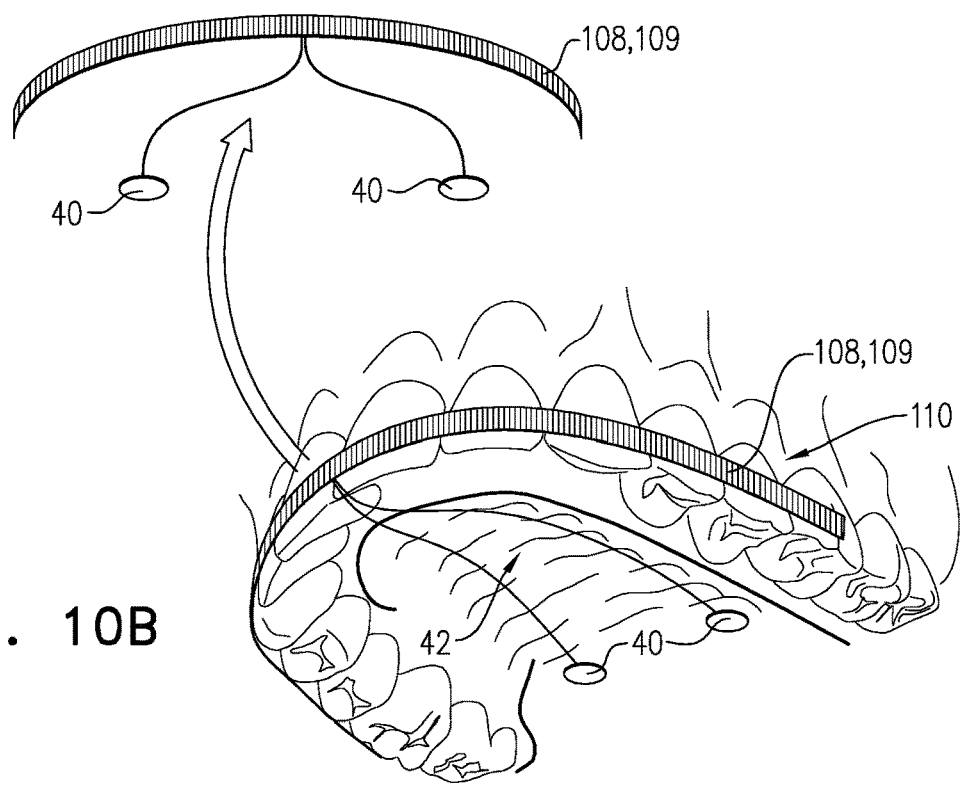

Reference is now made to FIGS. 10A-B, which show SPG stimulating device 20 in combination with at least one greater palatine foramen (GPF) electrode 40 coupled to a GPF electrode frame 108, e.g., a dental arch electrode frame 109 configured to be mounted to a dental arch 110 of patient 24, in accordance with some applications of the present invention. GPF electrode(s) 40 are coupled to control unit 26 and are couplable, using GPF electrode frame 108 (e.g., dental arch electrode frame 109) to hard palate 42 of patient 24 over a GPF 112 of patient 24. Control unit 26 drives electrode(s) 30 to stimulate SPG 22 by driving a current between electrode(s) 30 and at least one GPF electrode 40 (as illustrated by dashed current path 114).

Figure 11A:
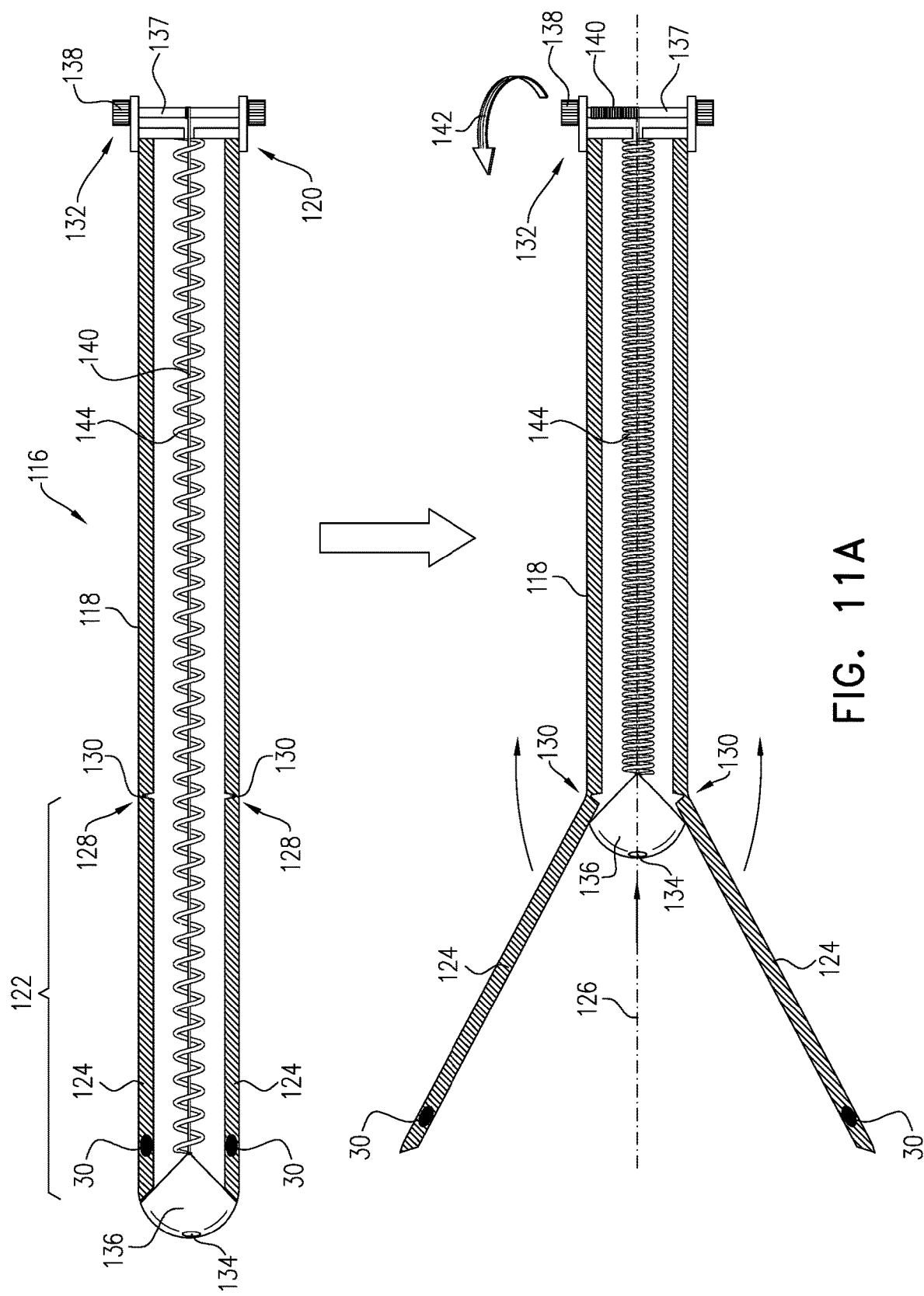

Reference is now made to FIGS. 11A-B, which are schematic illustrations of a nasal SPG stimulating device 116, in accordance with some applications of the present invention. SPG stimulating device 116 has a flexible housing 118, e.g., made from a flexible polymer, having a proximal end portion 120 and a distal end portion 122. Distal end portion 122 is configured to be placed within nose 28 of patient 24 and is shaped to define a plurality of electrode arms 124, e.g., exactly three electrode arms 124, configured to open outward away from a central longitudinal axis 126 of housing 118 during deployment of electrode arms 124. Each electrode arm 124 is coupled to flexible housing 118 at a proximal end 128 of electrode arm 124. For some applications, each electrode arm 124 is coupled to flexible housing 118 using a hinge 130, e.g., an integral hinge (such as is shown in FIGS. 11A-B), or a pivot hinge. For some applications, each electrode arm 124 is a flexible part of housing 118 that is configured to flex outwardly away from central longitudinal axis 126 during deployment of electrode arms 124.

A deployment actuator 132 is configured to actuate the deployment of electrode arms 124, further described hereinbelow. A camera 134, typically housed in a cone-shaped camera housing 136, is (a) disposed at distal end portion 122 of housing 118 prior to the deployment of electrode arms 124 and (b) configured to facilitate navigation of housing 118 toward SPG 22. As further described hereinbelow, proximal motion of camera 134 toward proximal end portion 120 of housing 118 is associated with, e.g., causes, the deployment of electrode arms 124. Coupled to each electrode arm 124 is at least one electrode 30 such that when distal end portion 122 is placed within nose 28 and electrode arm 124 is deployed, at least one electrode 30 is positioned to stimulate SPG 22. It is noted that the same reference number is used for the electrodes coupled to SPG stimulating device 116 as for electrodes coupled to SPG stimulating device 20 to indicate that the same type of electrodes may be used.

For some applications, deployment actuator 132 is a rotatable spool 137 disposed at a longitudinal location along housing 118, e.g., at proximal end portion 120 of housing 118, configured to be rotated using a knob 138. Camera housing 136 is attached to a string 140 that runs longitudinally through housing 118 and is configured to be wrapped around spool 137 when knob 138 is turned in a first direction, indicated by arrow 142. A spring 144 is disposed within housing 118 between camera housing 136 and proximal end portion 120 of housing such that proximal motion of camera housing 136 causes spring 144 to compress. SPG stimulating device 116 is positioned within nose 28 of patient 24 and then the medical practitioner rotates knob 138 so as to wind string 140 around spool 137, illustrated by arrow 142. As string 140 is wound around spool 137, camera housing 136 is pulled proximally, thereby causing spring 144 to compress. Due to the conical shape of camera housing 136, as camera housing 136 moves proximally, camera housing 136 forces electrode arms 124 to deploy outward.

FIG. 11B illustrates how electrode arms 124 of SPG stimulating device 116 are closed prior to removal of SPG stimulating device 116 from nose 28 of patient 24. In order to close electrode arms 124, the medical practitioner turns knob 138 in the opposite direction, illustrated by arrow 146, thus unwinding string 140 from spool 137. Due to the compressed state of spring 144, as string 140 is unwound from around spool 137, spring 144 pushes camera housing 136 distally thus allowing electrode arms 124 to close back to their initial starting position.

Figure 12A:
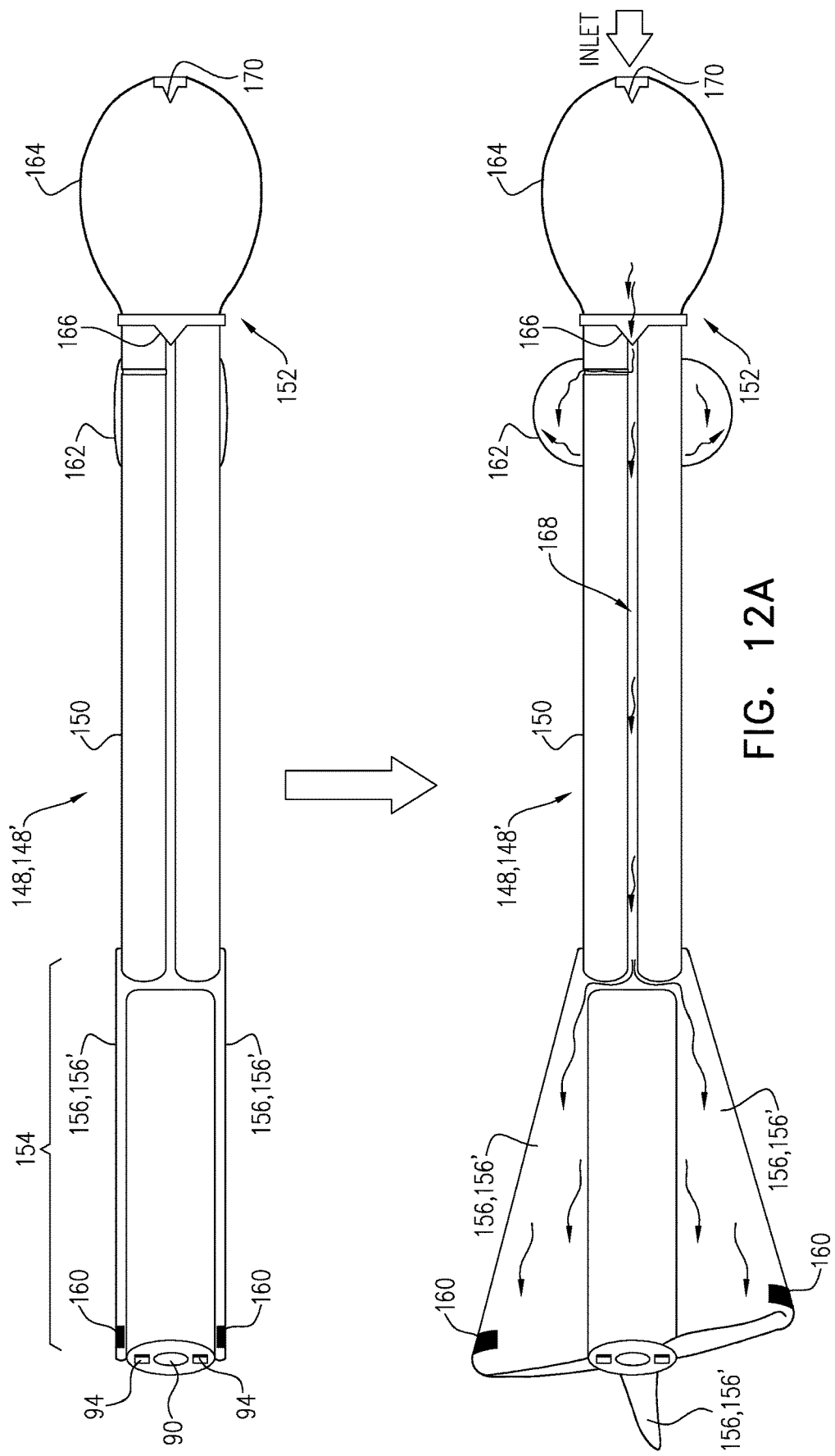
FIGS. 12A-B and 13 are schematic illustrations of different variations of a nasal SPG stimulating device, in accordance with some applications of the present invention.
Figure 12B:
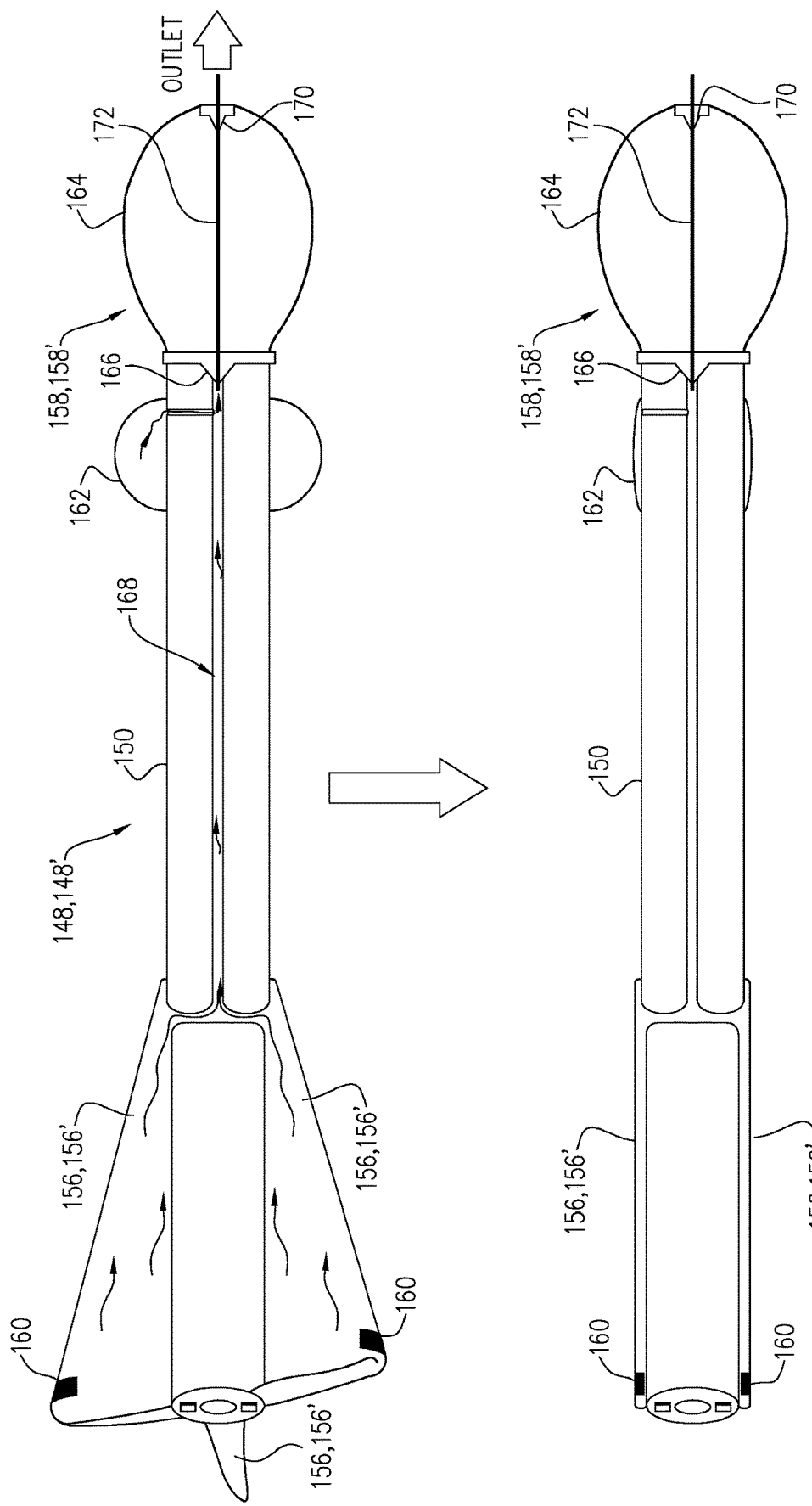
Figure 13:
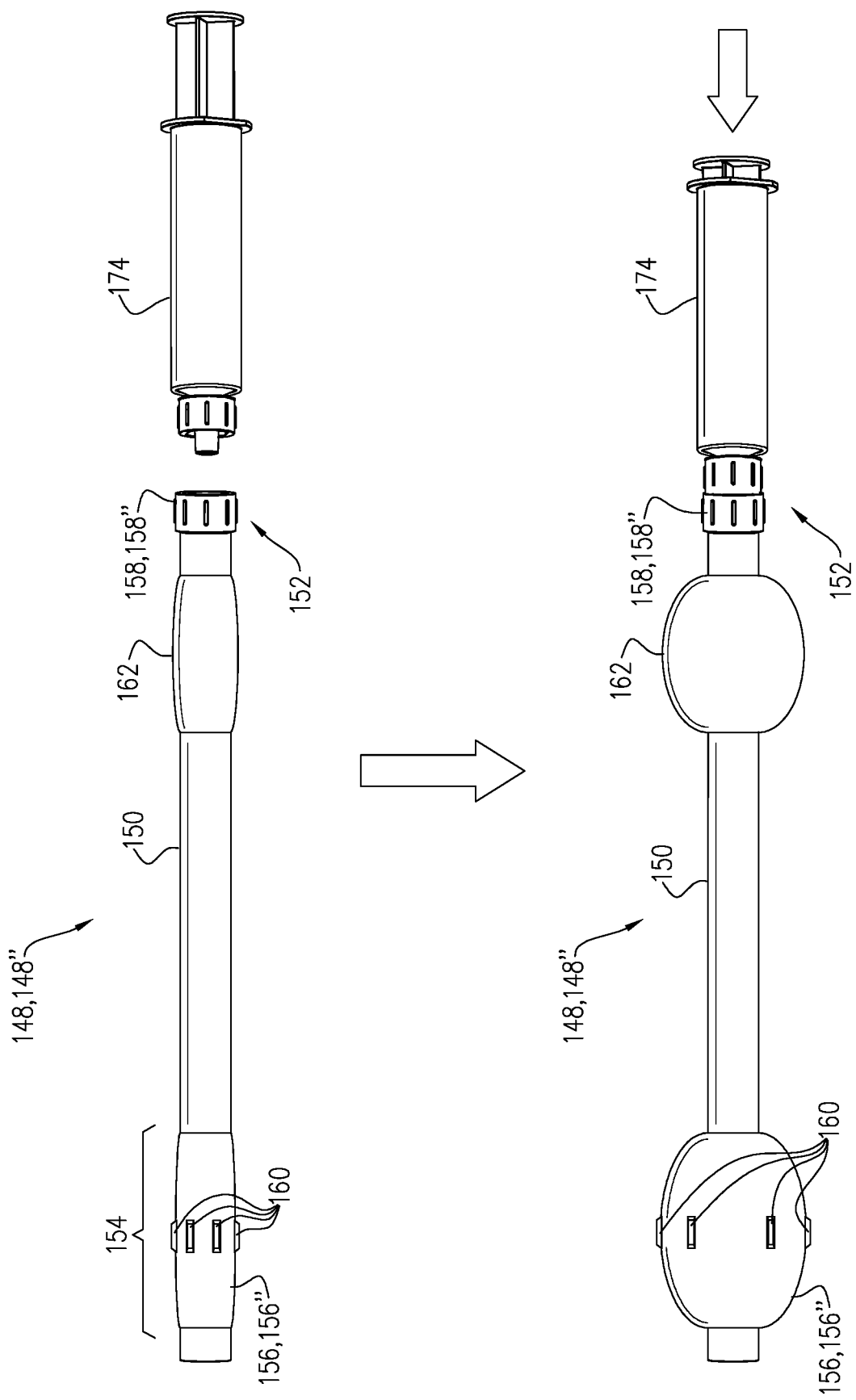

Reference is now made to FIGS. 12A-B and 13, which are schematic illustrations of a nasal SPG stimulating device 148, in accordance with some applications of the present invention. Nasal SPG stimulating device 148 includes a flexible tube 150 configured for placement within nose 28 of patient 24 and having a proximal end portion 152 and a distal end portion 154. Distal end portion 154 has at least one inflatable electrode mount 156, and proximal end portion 152 includes an inflation actuator 158 via which at least one inflatable electrode mount 156 is inflatable. At least one electrode 160, e.g., a plurality of electrodes 160, is coupled to inflatable electrode mount 156 such that when SPG stimulating device 148 is placed within nose 28 and inflatable electrode mount 156 is inflated, electrode 160 is positioned to stimulate SPG 22. For some applications, each electrode 160 comprises a specific area of inflatable electrode mount 156 made of a conductive polymer. Typically, SPG stimulating device 148 further includes an inflatable nasal stabilizer 162 disposed around flexible tube 150 and configured to stabilize flexible tube 150 with respect to nostril 60 of nose 28 when flexible tube 150 is disposed within nose 28 and inflatable nasal stabilizer 162 is inflated using inflation actuator 158. Similarly to SPG stimulating device 20, SPG stimulating device 148 also includes camera 90, e.g., a micro camera, or a fiber-optic camera, to facilitate navigation of the device toward SPG 22, and one or more light sources 94, e.g., LED light sources, in order to provide illumination for camera 90.

Reference is now made specifically to FIGS. 12A-B, which depict a particular variation SPG stimulating device 148', which is an implementation of SPG stimulating device 148, in accordance with some applications of the present invention. For some applications, SPG stimulating device 148' includes a plurality of inflatable electrode mounts 156', e.g., exactly three inflatable electrode mounts 156', positioned circumferentially around distal end portion 154 of flexible tube 150. A respective at least one electrode 160 is coupled to each of the respective inflatable electrode mounts 156'.

Inflation actuator 158' of SPG stimulating device 148' is in the form of a hand bulb pump. A hollow pumpable bulb 164 is disposed proximal end portion 152 of flexible tube 150. A first duckbill valve 166 allows air from within bulb 164 to enter an air-channel 168 that extends through flexible tube 150 when bulb 164 is squeezed. Air-channel 168 includes ports that allow air from within air-channel 168 to enter each inflatable electrode mount 156' and inflatable nasal stabilizer 162. As the squeezing of bulb 164 is released, a second duckbill valve 170 allows air from outside the device to enter bulb 164 in order to re-inflate bulb 164. Bulb 164 may thus be pumped one or more times in order to inflate inflatable electrode mounts 156' and inflatable nasal stabilizer 162. FIG. 12A shows the transition from (a) SPG stimulating device 148' prior to inflation (i.e., the form in which SPG stimulating device 148' is inserted into nose 28 of patient 24) to (b) SPG stimulating device 148' after inflation of inflatable electrode mounts 156' and inflatable nasal stabilizer 162. FIG. 12B illustrates the deflation of inflatable electrode mounts 156' and inflatable nasal stabilizer 162 prior to removal of SPG stimulating device 148' from nose 28. A narrow hollow rod 172, e.g., a needle, is inserted through the opening of both duckbill valve 177 and duckbill valve 166 in order to provide fluid communication between air-channel 168 and the environment, thus allowing inflatable electrode mounts 156' and inflatable nasal stabilizer 162 to deflate.

Reference is now made specifically to FIG. 13, which depicts SPG stimulating device 148", which is an implementation of SPG stimulating device 148, in accordance with some applications of the present invention. For some applications, the at least one inflatable electrode mount 156 is an inflatable electrode balloon 156" with a plurality of electrodes 160 positioned circumferentially around inflatable balloon 156" such that when SPG stimulating device 148" is placed within nose 28 of patient 24 and inflatable electrode balloon 156" is inflated, at least one of the plurality of electrodes 160 is positioned to stimulate SPG 22.

Inflation actuator 158" of SPG stimulating device 148" may be a Luer lock valve to which a Luer syringe 174 may be coupled. When Luer syringe 174 is coupled to the Luer lock valve, the valve is opened and gas or liquid may be injected into flexible tube 150 in order to inflate inflatable electrode balloon 156" and inflatable nasal stabilizer 162. When Luer syringe 174 is disconnected from the Luer lock valve, the valve self-seals. In order to deflate inflatable electrode balloon 156" and inflatable nasal stabilizer 162, Luer syringe 174 is re-coupled to the Luer lock valve and the injected gas or liquid escapes or is drawn out. For some applications, inflatable electrode balloon 156" and inflatable nasal stabilizer 162 may be inflated with an injection of contrast fluid. This may aid visualization of the positioning of SPG stimulating device 148" within nose 28 under fluoroscopy.

Figure 14A:
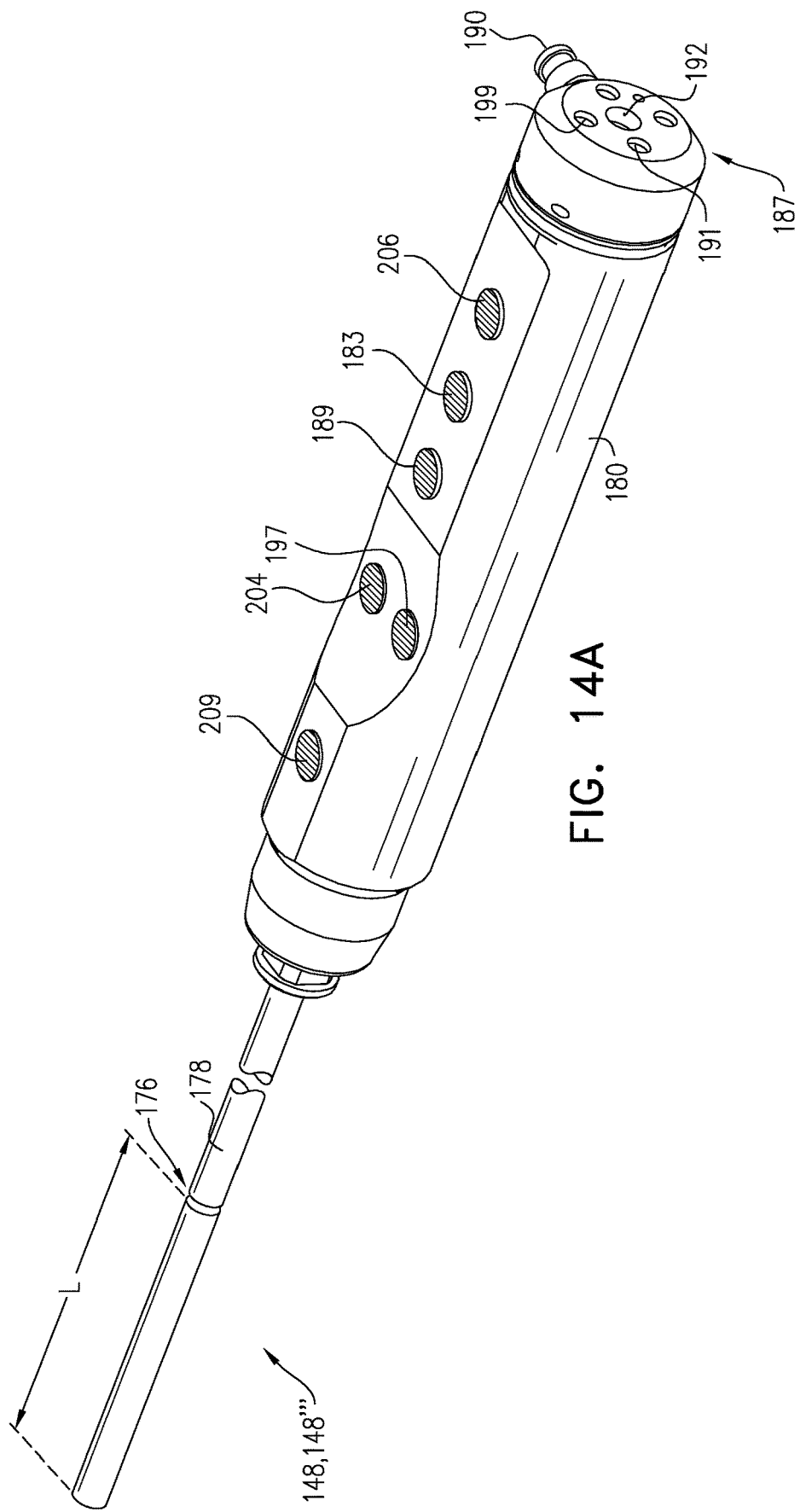
FIGS. 14A-C are schematic illustrations of a particular variation of a nasal SPG stimulating device, in accordance with some applications of the present invention.
Figure 14B:
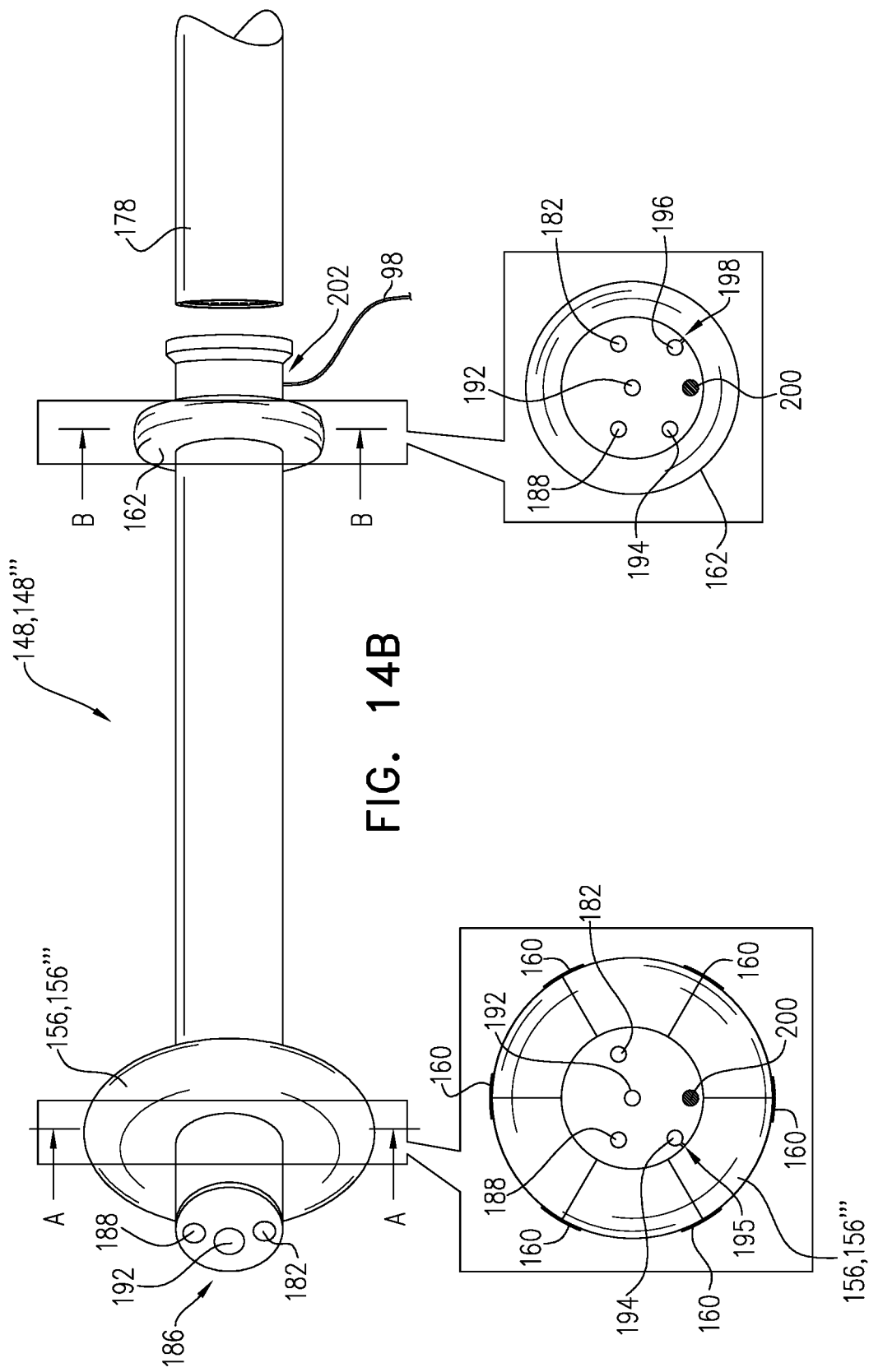
Figure 14C:
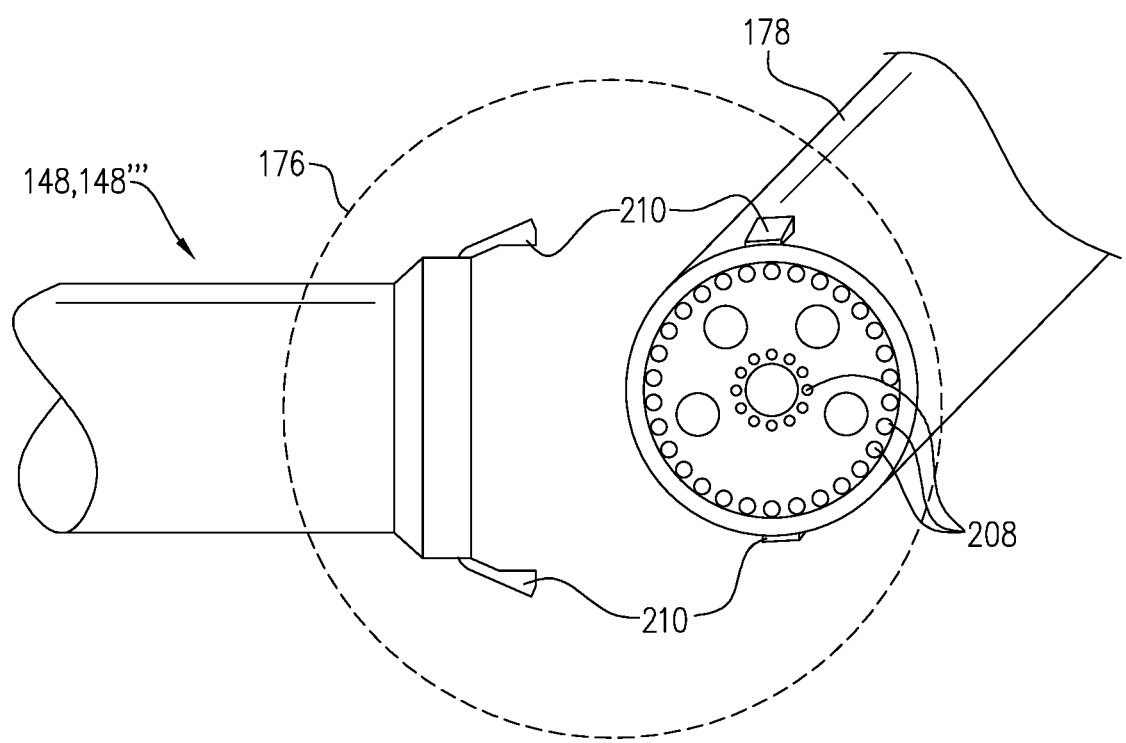

Reference is now made to FIGS. 14A-C, which are schematic illustrations of SPG stimulating device 148"', which is an implementation of SPG stimulating device 148, in accordance with some applications of the present invention. SPG stimulating device 148"' is an implantable unit connected (via a quick-connecter 176 further described hereinbelow) to a flexible catheter 178, e.g., a steerable catheter. For some applications, a diameter D4 of flexible catheter may be at least 3 mm and/or less than 8 mm. For some applications, a length L of the implantable unit may be at least 40 mm and/or less than 80 mm. An actuation handle 180 is disposed at a proximal end of flexible catheter 178. Similarly to SPG stimulating device 148", SPG stimulating device 148" has inflatable electrode balloon 156"' and inflatable nasal stabilizer 162. A plurality of channels extend from a proximal end 187 of actuation handle 180 through flexible catheter 178 to SPG stimulating device 148"'. The channels may include, for example, any combination of one or more of the following:

- an irrigation channel 182 (e.g., that ends at a distal tip 186 of SPG stimulating device 148"), the actuation of irrigation through irrigation channel 182 controlled by irrigation control 183 on actuator handle 180, and a proximal end 187 of actuator handle 180 including an irrigation connector 191 to connect handle 180 to a source of irrigation liquid;
- a suction channel 188 (e.g., that ends at distal tip 186), the actuation of suction through suction channel 188 controlled by suction control 189 on actuator handle 180, and proximal end 187 of actuator handle 180 including a suction port 190 for connecting handle 180 to a source of vacuum;
- an endoscope channel 192 that starts from proximal end 187 of handle and extends through to distal tip 186, through which an endoscope can be inserted to aid in navigation of SPG stimulating device 148" toward SPG 22 of patient 24, actuator handle 180 including an endoscope control 206;
- an electrode balloon inflation channel 194 that extends to inflatable electrode balloon 156" and includes an electrode balloon two-way port 195 that enables fluid communication between electrode balloon inflation channel 194 and inflatable electrode balloon 156" for inflation and deflation of inflatable electrode balloon 156" (illustrated by cross-section A-A in FIG. 14B), the inflation and deflation of inflatable electrode balloon 156" controlled by electrode balloon control 197 on actuator handle 180, and proximal end 187 of actuator handle 180 including an air-port 199 connecting handle 180 to a source of air for inflation; and
- a nasal stabilizer inflation channel 196 that extends to inflatable nasal stabilizer 162 and includes a nasal stabilizer two-way port 198 that enables fluid communication between nasal balloon channel 196 and inflatable nasal stabilizer 162 for inflation and deflation of inflatable nasal stabilizer 162 (illustrated by cross-section B-B in FIG. 14B), the inflation and deflation of inflatable nasal stabilizer 162 controlled by nasal stabilizer control 204 on actuator handle 180, and proximal end 187 of actuator handle 180 including air-port 199 connecting handle 180 to a source of air for inflation.

An electrode-lead channel 200 for electrode leads 98 extends from inflatable electrode balloon 156" to a lead-exit hole 202 on a lateral side of SPG stimulating device 148"'. FIG. 14C illustrates connector 176 between SPG stimulating device 148"' and flexible catheter 178. For some applications, connector 176 is a face-seal connector, i.e., it connects two components face-to-face with no overlap between the components. A pneumatic seal is activated between SPG stimulating device 148' and flexible catheter 178 via a plurality of suction micro-channels 208 at connector 176. An alignment facilitator 210 allows the medical practitioner to align SPG stimulating device 148" and flexible catheter 178 correctly with respect to each other so that the respective channels line up correctly, and subsequently suction is applied through micro-channels 208 in order to seal the connection between SPG stimulating device 148" and flexible catheter 178. Once SPG stimulating device 148" has been positioned correctly within nose 28 (and the endoscope removed in cases where an endoscope is fed through endoscope channel 192), the suction through micro-channels 208 may be terminated in order to disconnect flexible catheter 178 from SPG stimulating device 148". Suction through micro-channels 208 is controlled by connector control 209 on actuator handle 180. It is noted that the pneumatic face-seal connector described herein is just one example of a connector between SPG stimulating device 148" and flexible catheter 178, and is not intended to be limiting. Any type of connector that maintains connection between SPG stimulating device 148" and flexible catheter 178 during positioning of SPG stimulating device 148' and can then subsequently be disconnected may be used.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A sphenopalatine ganglion (SPG) stimulating device for stimulating an SPG of a patient, the device comprising:
   a sheath having a proximal end portion and a distal end portion, the distal end portion shaped to define at least one electrode opening;
   a nasal stabilizer disposed around the sheath and configured to stabilize the sheath with respect to a nostril of a nose of the patient when the sheath is disposed within the nose;
   an electrode mount, slidably disposed within the sheath;
   at least one electrode coupled to the electrode mount and deployable out of the sheath through the at least one electrode opening to position the at least one electrode to stimulate the SPG;
   a control unit comprising a battery and circuitry and configured to drive the at least one electrode to stimulate the SPG; and
   a sensor configured to sense a physiological response of the patient to stimulation of the SPG and to send to the control unit a signal indicative of the physiological response.

2. The device according to claim 1, wherein the sheath is flexible.

3. The device according to claim 1, wherein a distance between the nasal stabilizer and the at least one electrode opening is 4-8 cm.

4. The device according to claim 1, wherein an outer diameter of the nasal stabilizer is 3-15 mm greater than an outer diameter of the sheath.

5. The device according to claim 1, wherein an outer diameter of the sheath is 3-8 mm.

6. The device according to claim 1, wherein the at least one electrode is configured to curve away from a central longitudinal axis of the sheath during deployment of the at least one electrode.

7. The device according to claim 1, wherein the nasal stabilizer is connected to the sheath.

8. The device according to claim 1, wherein the at least one electrode is arranged such that distal motion of the electrode mount with respect to the sheath deploys the at least one electrode out of the sheath through the at least one electrode opening.

9. The device according to claim 8, wherein the nasal stabilizer is arranged to remain in a same location with respect to the sheath during the distal motion of the electrode mount with respect to the sheath.

10. The device according to claim 9, further comprising a releasable post-deployment lock, configured to prevent sliding of the electrode mount within the sheath following the distal motion of the electrode mount with respect to the sheath.

11. The device according to claim 1, wherein the at least one electrode is arranged such that proximal motion of the sheath with respect to the electrode mount deploys the at least one electrode out of the sheath through the at least one electrode opening.

12. The device according to claim 11, wherein the sheath is arranged to slide proximally with respect to the nasal stabilizer during the proximal motion of the sheath with respect to the electrode mount.

13. The device according to claim 12, wherein the sheath is shaped to define a longitudinal slit on a lateral side of the sheath, and wherein the nasal stabilizer is connected to the electrode mount through the longitudinal slit.

14. The device according to claim 1, wherein the sensor is coupled to the sheath.

15. The device according to claim 14, wherein the sensor is a Doppler flowmetry sensor.

16. The device according to claim 1, wherein the sensor is coupled to the electrode mount, and wherein the sensor is a Doppler flowmetry sensor.

17. The device according to claim 1, further comprising a camera coupled to the sheath and configured to facilitate navigation of the sheath toward the SPG.

18. The device according to claim 1, further comprising a camera fixed to a distal end of the electrode mount, configured to facilitate navigation of the distal end of the electrode mount toward the SPG.

19. The device according to claim 1, wherein the control unit is wearable.

20. The device according to claim 1, wherein the at least one electrode comprises a plurality of electrodes, and wherein the control unit is configured to designate at least one of the plurality of electrodes to exclude from use for stimulating the SPG in response to the signal.

21. The device according to claim 1, wherein the sensor is a Doppler flowmetry sensor, and wherein the Doppler flowmetry sensor is configured to be coupled to skin of the patient over a carotid artery of the patient.

22. A sphenopalatine ganglion (SPG) stimulating device for stimulating an SPG of a patient, the device comprising:
   a sheath having a proximal end portion and a distal end portion, the distal end portion shaped to define at least one electrode opening;
   a nasal stabilizer disposed around the sheath and configured to stabilize the sheath with respect to a nostril of a nose of the patient when the sheath is disposed within the nose;
   an electrode mount, slidably disposed within the sheath; and
   at least one electrode coupled to the electrode mount and deployable out of the sheath through the at least one electrode opening to position the at least one electrode to stimulate the SPG;
   wherein a distance between the nasal stabilizer and the at least one electrode opening is 4-8 cm.

23. The device according to claim 22, wherein the nasal stabilizer is connected to the sheath.

24. The device according to claim 22, wherein the at least one electrode is arranged such that distal motion of the electrode mount with respect to the sheath deploys the at least one electrode out of the sheath through the at least one electrode opening.

25. The device according to claim 22, wherein the at least one electrode is arranged such that proximal motion of the sheath with respect to the electrode mount deploys the at least one electrode out of the sheath through the at least one electrode opening.

26. A sphenopalatine ganglion (SPG) stimulating device for stimulating an SPG of a patient, the device comprising:
   a sheath having a proximal end portion and a distal end portion, the distal end portion shaped to define at least one electrode opening;
   a nasal stabilizer disposed around the sheath and configured to stabilize the sheath with respect to a nostril of a nose of the patient when the sheath is disposed within the nose;

an electrode mount, slidably disposed within the sheath; and at least one electrode coupled to the electrode mount and deployable out of the sheath through the at least one electrode opening to position the at least one electrode to stimulate the SPG:

wherein an outer diameter of the nasal stabilizer is 3-15 mm greater than an outer diameter of the sheath.

27. The device according to claim 26, wherein the nasal stabilizer is connected to the sheath.

28. The device according to claim 26, wherein the at least one electrode is arranged such that distal motion of the electrode mount with respect to the sheath deploys the at least one electrode out of the sheath through the at least one electrode opening.

29. The device according to claim 26, wherein the at least one electrode is arranged such that proximal motion of the sheath with respect to the electrode mount deploys the at least one electrode out of the sheath through the at least one electrode opening.

30. A sphenopalatine ganglion (SPG) stimulating device for stimulating an SPG of a patient, the device comprising:

a sheath having a proximal end portion and a distal end portion, the distal end portion shaped to define at least one electrode opening;

a nasal stabilizer disposed around the sheath and configured to stabilize the sheath with respect to a nostril of a nose of the patient when the sheath is disposed within the nose;

an electrode mount, slidably disposed within the sheath; and at least one electrode coupled to the electrode mount and deployable out of the sheath through the at least one electrode opening to position the at least one electrode to stimulate the SPG:

wherein an outer diameter of the sheath is 3-8 mm.

31. The device according to claim 30, wherein the nasal stabilizer is connected to the sheath.

32. The device according to claim 30, wherein the at least one electrode is arranged such that distal motion of the electrode mount with respect to the sheath deploys the at least one electrode out of the sheath through the at least one electrode opening.

33. The device according to claim 30, wherein the at least one electrode is arranged such that proximal motion of the sheath with respect to the electrode mount deploys the at least one electrode out of the sheath through the at least one electrode opening.

34. A sphenopalatine ganglion (SPG) stimulating device for stimulating an SPG of a patient, the device comprising:

a sheath having a proximal end portion and a distal end portion, the distal end portion shaped to define at least one electrode opening;

a nasal stabilizer disposed around the sheath and configured to stabilize the sheath with respect to a nostril of a nose of the patient when the sheath is disposed within the nose;

an electrode mount, slidably disposed within the sheath; and at least one electrode coupled to the electrode mount and deployable out of the sheath through the at least one electrode opening to position the at least one electrode to stimulate the SPG:

wherein the at least one electrode is configured to curve away from a central longitudinal axis of the sheath during deployment of the at least one electrode.

35. The device according to claim 34, wherein the nasal stabilizer is connected to the sheath.

36. The device according to claim 34, wherein the at least one electrode is arranged such that distal motion of the electrode mount with respect to the sheath deploys the at least one electrode out of the sheath through the at least one electrode opening.

37. The device according to claim 34, wherein the at least one electrode is arranged such that proximal motion of the sheath with respect to the electrode mount deploys the at least one electrode out of the sheath through the at least one electrode opening.

38. A sphenopalatine ganglion (SPG) stimulating device for stimulating an SPG of a patient, the device comprising:

a sheath having a proximal end portion and a distal end portion, the distal end portion shaped to define at least one electrode opening;

a nasal stabilizer disposed around the sheath and configured to stabilize the sheath with respect to a nostril of a nose of the patient when the sheath is disposed within the nose;

an electrode mount, slidably disposed within the sheath;

at least one electrode coupled to the electrode mount and deployable out of the sheath through the at least one electrode opening to position the at least one electrode to stimulate the SPG; and a sensor coupled to the electrode mount and configured to sense a physiological response of the patient to stimulation of the SPG, wherein the sensor is a Doppler flowmetry sensor.

39. The device according to claim 38, wherein the nasal stabilizer is connected to the sheath.

40. The device according to claim 38, wherein the at least one electrode is arranged such that distal motion of the electrode mount with respect to the sheath deploys the at least one electrode out of the sheath through the at least one electrode opening.

41. The device according to claim 38, wherein the at least one electrode is arranged such that proximal motion of the sheath with respect to the electrode mount deploys the at least one electrode out of the sheath through the at least one electrode opening.

42. A sphenopalatine ganglion (SPG) stimulating device for stimulating an SPG of a patient, the device comprising:

a sheath having a proximal end portion and a distal end portion, the distal end portion shaped to define at least one electrode opening;

a nasal stabilizer disposed around the sheath and configured to stabilize the sheath with respect to a nostril of a nose of the patient when the sheath is disposed within the nose;

an electrode mount, slidably disposed within the sheath;

at least one electrode coupled to the electrode mount and deployable out of the sheath through the at least one electrode opening to position the at least one electrode to stimulate the SPG; and a control unit comprising a battery and circuitry and configured to drive the at least one electrode to stimulate the SPG, wherein the control unit is wearable.

43. The device according to claim 42, wherein the nasal stabilizer is connected to the sheath.

44. The device according to claim 42, wherein the at least one electrode is arranged such that distal motion of the electrode mount with respect to the sheath deploys the at least one electrode out of the sheath through the at least one electrode opening.

45. The device according to claim 42, wherein the at least one electrode is arranged such that proximal motion of the sheath with respect to the electrode mount deploys the at least one electrode out of the sheath through the at least one electrode opening.

\* \* \* \* \*